US008575093B2

(12) United States Patent
Mizrachi Nebenzahl et al.

(10) Patent No.: US 8,575,093 B2
(45) Date of Patent: Nov. 5, 2013

(54) **COMPOSITION AND METHOD FOR TREATING *STREPTOCOCCUS PNEUMONIAE* INFECTION**

(75) Inventors: Yaffa Mizrachi Nebenzahl, Be'er Sheva (IL); Ron Dagan, Omer (IL)

(73) Assignees: Ben-Gurion University of the Negev Research and Development Authority, Beer-Sheva (IL); Mor Research Applications Ltd., Tel-Aviv (IL)

( * ) Notice: Subject to any disclaimer, the term of this patent is extended or adjusted under 35 U.S.C. 154(b) by 705 days.

(21) Appl. No.: 12/285,115

(22) Filed: Sep. 29, 2008

(65) Prior Publication Data

US 2009/0186043 A1 Jul. 23, 2009

Related U.S. Application Data

(63) Continuation-in-part of application No. PCT/IL2007/000421, filed on Mar. 29, 2007.

(60) Provisional application No. 60/787,163, filed on Mar. 30, 2006.

(51) Int. Cl.
*A61K 38/00* (2006.01)
*C07K 16/00* (2006.01)

(52) U.S. Cl.
USPC .............................. 514/2.6; 530/326; 530/327

(58) Field of Classification Search
None
See application file for complete search history.

(56) References Cited

U.S. PATENT DOCUMENTS 5,958,729 A * 9/1999 Soppet et al. ................. 435/69.1
2004/0031072 A1 2/2004 La Rosa et al.

FOREIGN PATENT DOCUMENTS

| WO | WO 96/39439 | 12/1996 |
| WO | 03/982183 | 10/2003 |
| WO | WO 03/082183 | 10/2003 |
| WO | WO 2007/113819 | 10/2007 |

OTHER PUBLICATIONS

Ofek et al (FEMS Immunology and Medical Microbiology 38:181-191, 2003).*
Bavington et al (Respiration, 72:335-344, 2005.*
Hammerschmidt et al (J. Immunology, 178:5848-5858, 2007.*
Rudinger et al, in "Peptide Hormones", edited by Parsons, J.A., University Park Press, Jun. 1976, p. 6.*
Burgess et al., The Journal of Cell Biology, 111:2129-2138, 1990.*
Lazar et al., Molecular and Cellular Biology, 8(3):1247-1252, 1988.*
Jobling et al. (Mol. Microbiol., 1991, 5(7):1755-67.*
NCBI Accession No. Q9NYQ7, human Flamingo homolog 1; First accessible on Jun. 15, 2002.*
Sharon et al., Glycoconjugate Journal, 17:659-644, 2000.*

Communication Pursuant to Rules 161 and 162 EPC Dated Jun. 10, 2009 From the European Patent Office Re. Application No. 07736161.6.
Communication Pursuant to Rules 70(2) and 70a(2) EPC Dated Aug. 20, 2010 From the European Patent Office Re. Application No. 07736161.6.
International Preliminary Report on Patentability Dated Mar. 10, 2009 From the International Bureau of WIPO Re. Application No. PCT/IL2007/000421.
Office Action Dated Apr. 5, 2009 From the Israel Patent Office Re. Application No. 194372.
Office Action Dated Nov. 10, 2010 From the Israel Patent Office Re. Application No. 194372.
Response Dated Jan. 3, 2010 to Office Action of Apr. 5, 2009 From the Israel Patent Office Re. Application No. 194372.
Supplementary European Search Report and the European Search Opinion Dated Aug. 3, 2010 From the European Patent Office Re. Application No. 07736161.6.
Bäckhed et al. "Identification of Target Tissue Glycosphingolipid Receptors for Uropathogenic, F1C-Fimbriated *Escherichia coli* and Its Role in Mucosal Inflammation", The Journal of Biological Chemistry, 277(20): 18198-18205, May 17, 2002.
Blau et al. "Flamingo Cadherin A Putative Target for Protective Autoimmunity to *Streptococcus pneumoniae* (Pnc)", VIAMR, Lausanne Switzerland, Oct. 26-28, 2005. Abstract.
Blau et al. "Flamingo Cadherin: A Putative Host Receptor for *Streptococcus pneumoniae*", Journal of Infectious Diseases, XP002592490, 195(12): 1828-1837, Jun. 2007.
Blau et al. "Hunt for *Streptococcus pneumoniae* (Pnc) Adhesion Inhibitors: Implementation of Phage Display Analysis of Pnc Cell Wall Lection (CW-L) Proteins", Unpublished, Abstract.
Blau et al. "Identification of A Novel S Pneumoniae (Pnc) Adhesin and Its Human Putative Receptors", Unpublished, Jan. 29, 2005. Abstract.
Blau et al. "The Use of Phage Display Analysis of *Streptococcus pneumoniae* (Pnc) Cell Wall Lectin (CW-L) Proteins for Identification of Inhibitors of Pnc Adhesion to Host Mucosa", ISPPD, Helsinki, Finland, 2004. Abstract.
Enshell-Seijffers et al. "The Rational Design of a 'Type 88' Genetically Stable Peptide Display Vector in the Filamentous Bacteriophage FD", Nucleic Acids Research, 29(10/e50): 1-13, 2001.
Lambert de Rouvroit et al. "The Celsr 3 (Flamingo) Cadherin Interacts With Alpha-Actinin-2", Abstract of the Annual Meeting of the Society for Neuroscience, Washington, DC, USA, Nov. 10, 2003, XP009136318, Presentation No. 350.1, Nov. 8, 2003.
Ling et al. "Glycolytic Enzymes Associated With the Cell Surface of *Streptococcus pneumoniae* Are Antigenic in Humans and Elicit Protective Immune Responses in the Mouse", Clinical and Experimental Immunology, 138: 290-298, 2004.
Ling et al. "*S. pneumoniae* (Pnc) Glycolytic Enzymes Are Immunogenic in Humans and Elicit Protective Level Immune Responses in Mice", Unpublished, Dec. 31, 2003. Abstract.
Ling et al. "*S. pneumoniae* (Pnc) Surface Proteins as Modulators of Host Resonse", Unpublished, Abstract.

(Continued)

*Primary Examiner* — Patricia A Duffy

(57) ABSTRACT

A method of preventing and/or treating *S. pneumoniae* infection in mammalian subjects, wherein said method comprises administering to said subjects a composition comprising one or more agents that are capable of inhibiting the binding of the *S. pneumoniae* cell wall protein FBA to the respiratory tract cells of said subject.

5 Claims, 24 Drawing Sheets

(56) References Cited

OTHER PUBLICATIONS

Ling et al. "*Streptococcus pneumoniae* Cell Wall (CW) Associated Glycolytic Enzymes as Vaccine Candidates", Unpublished, Abstract.
Ling et al. "Vaccine Potential of *S. Pneumoniae* (Pnc) Surface Proteins", Unpublished, Abstract.
Merrifield "Solid Phase Peptide Synthesis. I. The Synthesis of A Tetrapeptide", Journal of the American Chemical Society, JACS, 85(14): 2149-2154, Jul. 20, 1963.
Mizeachi Nebenzahl et al. "Vaccine Potential of *S. pneumoniae* (Pnc) Surface Proteins", Unpublished, Abstract.
Mizrachi Nebenzahl et al. "Virulence of *Streptococcus pneumoniae* May Be Determined Independently of Capsular Polysaccharide", FEMS Microbiology Letters, 233: 147-152, 2004.
Portnoi et al. "Differential Expression of *Streptococcus pneumoniae* (Pnc) Cell Wall Proteins (CWP) in Virulent and Non Virulent Strains", Unpublished, Abstract.
Portnoi et al. "Proteomics of *Streptococcus pneumoniae* (Pnc) Surface Proteins Display Differential Expression of Proteins in Virulent and Non Virulent Strains", Unpublished, Dec. 31, 2003. Abstract.
Portnoi et al. "The Vaccine Potential of *Streptococcus pneumoniae* Surface Lectin- and Non-Lectin Proteins", Vaccine, 24(11): 1868-1873, Mar. 10, 2006.
Tissir et al. "Protocadherin Celsr3 Is Crucial in Axonal Tract Development", Nature Neuroscience, XP002592489, 8(4): 451-457, Apr. 2005. Abstract.
Office Action Dated Sep. 19, 2012 From the Israel Patent Office Re. Application No. 194372 and Its Translation Into English.
Response Dated Feb. 7, 2011 to Supplementary European Search Report and the European Search Opinion of Aug. 3, 2010 From the European Patent Office Re. Application No. 07736161.6.
Response Dated Mar. 10, 2011 to Office Action of Nov. 10, 2010 From the Israel Patent Office Re. Application No. 194372.
Communication Under Rule 71(3) EPC Dated Jun. 27, 2012 From the European Patent Office Re. Application No. 07736161.6.
International Search Report for PCT/IL2007/000421, mailed Apr. 25, 2008.
Written Opinion of the International Searching Authority for PCT/IL2007/000421, mailed Apr. 25, 2008.
Communication Pursuant to Article 94(3) EPC Dated Sep. 12, 2011 From the European Patent Office Re. Application No. 07736161.6.
Invitation Pursuant to Article 94(3) and Rule 71(1) EPC Dated Feb. 9, 2012 From the European Patent Office Re. Application No. 07736161.6.

\* cited by examiner

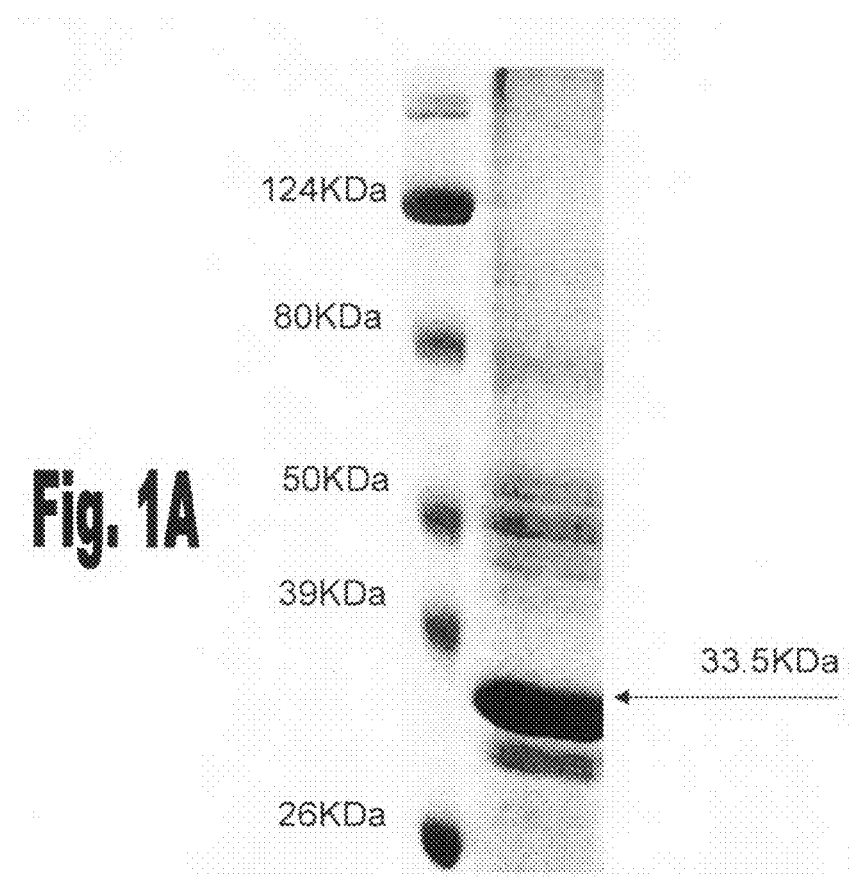
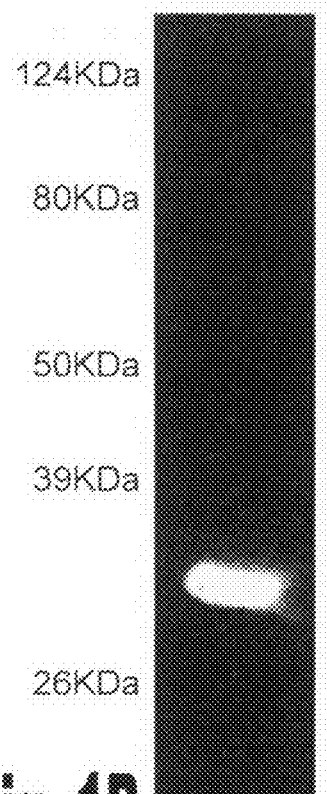
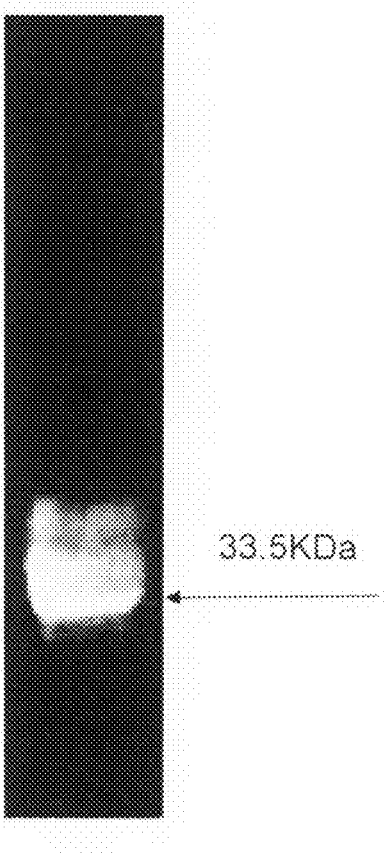

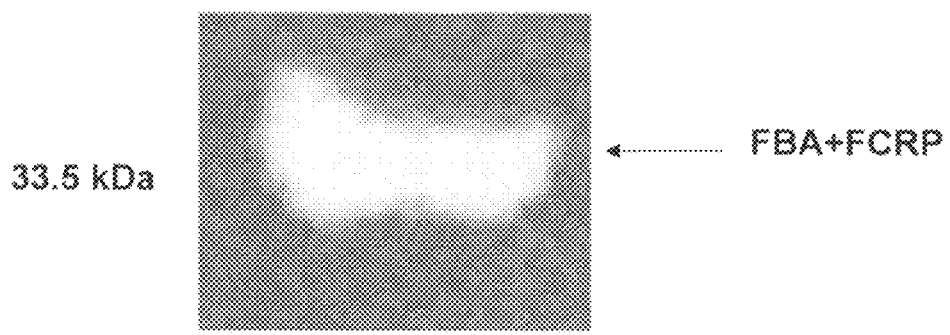
33.5 kDa — FBA+FCRP
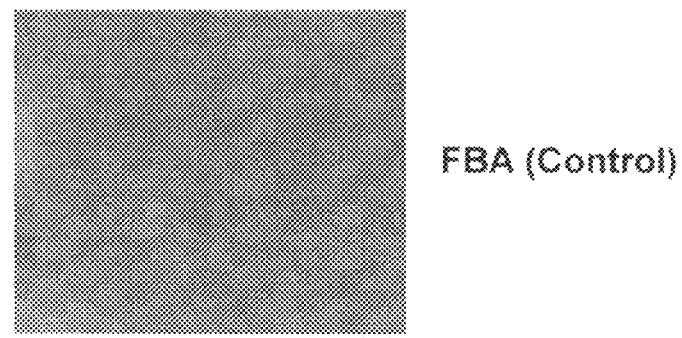
FBA (Control)
Fig. 7C
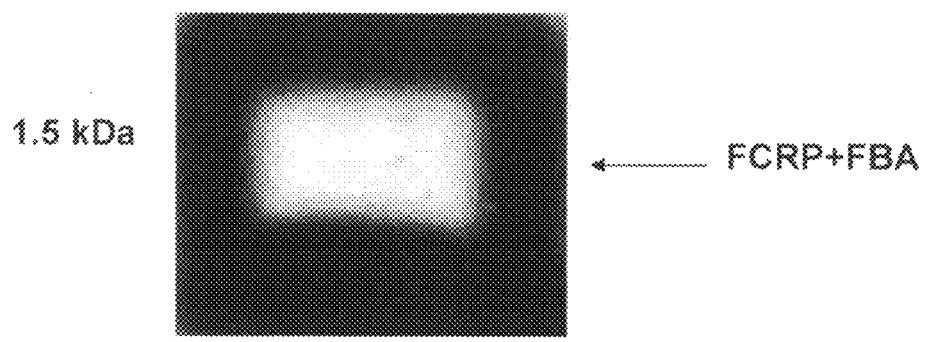
1.5 kDa — FCRP+FBA
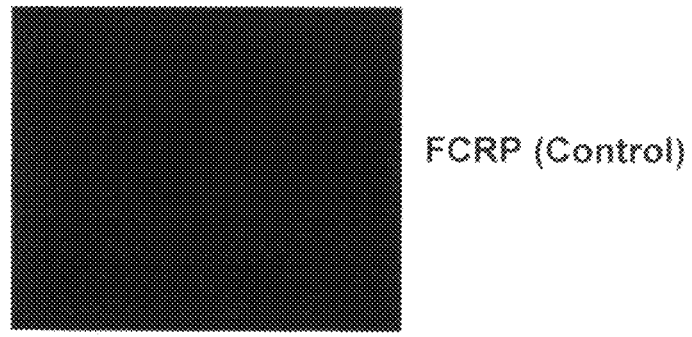
FCRP (Control)
Fig. 7D

SEQUENCE LISTING

```
<160> NUMBER OF SEQ ID NOS: 5

<210> SEQ ID NO 1
<211> LENGTH: 13
<212> TYPE: PRT
<213> ORGANISM: Homo sapiens

<400> SEQUENCE: 1

Asp Ser Asp Ser Asp Ser Asp Leu Ser Leu Glu Glu Glu
1               5                   10

<210> SEQ ID NO 2
<211> LENGTH: 15
<212> TYPE: PRT
<213> ORGANISM: Homo sapiens

<400> SEQUENCE: 2

Ala Asp Ser Asp Ser Asp Ser Asp Leu Ser Leu Glu Glu Glu Arg
1               5                   10                  15

<210> SEQ ID NO 3
<211> LENGTH: 26
<212> TYPE: DNA
<213> ORGANISM: Artificial Sequence
<220> FEATURE:
<223> OTHER INFORMATION: synthetic forward primer

<400> SEQUENCE: 3
ggatccttga aaagaagga actatc                                          26

<210> SEQ ID NO 4
<211> LENGTH: 26
<212> TYPE: DNA
<213> ORGANISM: Artificial Sequence
<220> FEATURE:
<223> OTHER INFORMATION: synthetic reverse primer

<400> SEQUENCE: 4
gaattccaat tcttccttgt agtcgt                                         26

<210> SEQ ID NO 5
<211> LENGTH: 19
<212> TYPE: DNA
<213> ORGANISM: Artificial Sequence
<220> FEATURE:
<223> OTHER INFORMATION: synthetic forward primer
```

```
<400> SEQUENCE: 5
tttcacgttg aaaatctcc                                              19
```

COMPOSITION AND METHOD FOR TREATING *STREPTOCOCCUS PNEUMONIAE* INFECTION

This application is a Continuation-In-Part of International Application No. PCT/IL2007/000421, filed 29 Mar. 2007, which designated the U.S. and claims the benefit of U.S. Provisional Application No. 60/787,163, filed 30 Mar. 2006, the entire contents of each of which are hereby incorporated by reference.

FIELD OF THE INVENTION

The present invention relates to compositions and methods for use in preventing and treating infection of mammalian subjects by *Streptococcus pneumoniae*. More specifically, the present invention provides various compositions that may be used to prevent the adhesion of *S. pneumoniae* to mammalian host cells.

BACKGROUND OF THE INVENTION

*S. pneumoniae* is a gram-positive bacterial organism that colonizes the upper respiratory tract and causes life-threatening diseases such as pneumonia, bacteremia and meningitis throughout the world. Currently, more than one million children die each year from pneumococcal-associated diseases.

*S. pneumoniae* colonizes the nasopharynx asymptomatically, leading to a clinically-silent carriage state. Carriage is most prevalent in children and about 70-80% of children attending day care centers carry *S. pneumoniae* at any given time. In adults, the carriage rate may vary according to environmental conditions. The pathogenic mechanisms that convert this benign state of carriage into clinical disease are unknown. It is generally assumed, however, that in common with other bacterial species, development of the carriage state is dependent on recognition of host cells by *S. pneumoniae* and attachment thereto. It is also suspected that either the appearance of a new strain, unfamiliar to the immune system, or activation of the immune system, with another viral or bacterial pathogen, enables the invasion and spread of the bacteria into sterile tissues thereby converting the benign carriage state into a life-threatening or potentially life-threatening clinical disease.

Following attachment, the bacteria may invade the cells and tissues, thereby leading to the aforementioned disease states associated with *S. pneumoniae*. Bacterial attachment involves interaction between one or more bacterial surface proteins, known as adhesins, and one or more host cell receptors. By means of blocking the recognition and attachment stage it may be possible to prevent the carriage stage and hence avert the development of the abovementioned disease states. Identification of bacterial adhesins involved in attachment to host mucosal layer are of prime interest in understanding the molecular basis of bacterial interaction with the host.

Currently, there is growing resistance of *S. pneumoniae* to antibiotics. In addition, the currently available vaccines offer only limited protection against infection with this organism. Consequently, an urgent need exists for clinically-safe and efficacious methods of preventing the adhesion of *S. pneumoniae* to host cells.

SUMMARY OF THE INVENTION

The inventors have now found that fructose bisphosphate aldolase (FBA) functions as a bacterial adhesin, and advantageously, lacks human orthologs. In addition, the inventors have also found that it is possible to prevent the infection of a mammalian subject with *S. pneumoniae*, and/or treat a pre-existing infection due to this bacterium, by means of administering an agent that is capable of inhibiting the binding of the *S. pneumoniae* cell wall protein FBA to the respiratory tract cells of said subject.

It is to be understood that the aforementioned agent may be any agent that is capable of interfering with the binding of FBA to its receptor(s) in the mammalian host cells. Consequently, in one aspect of the present invention, said agent may be a compound or composition that binds to the FBA binding site (or receptor) on the host cells, for example FBA itself, a modified form of FBA (including mutant forms, chemically modified forms, fusion proteins comprising FBA or portions thereof), domains and subdomains of FBA and fragments of FBA. Alternatively, the aforementioned agent may be a compound or composition that prevents the bacterial cell-mammalian cell adhesion by means of binding to the FBA that is present on the *S. pneumoniae* cell wall. Such agents include (but not limited to) antibodies directed to one or more epitopes present on the FBA molecule, peptides having sequence identity or homology to one or more regions of the mammalian protein to which FBA binds (i.e. the FBA receptor) and soluble forms of the FBA receptor itself (including truncated forms, chemically modified forms, mutations and so on). It is to be emphasized that the terms 'FBA receptor' and 'FBA binding partner' are used herein to refer to any protein or other molecule or molecular assembly present in or on the host cells to which FBA is capable of binding.

The present invention is thus primarily directed to a method for preventing and/or treating *S. pneumoniae* infection in mammalian subjects by means of administering to said subjects a composition comprising one or more agents that are capable of inhibiting, reversing or preventing the binding of the *S. pneumoniae* cell wall protein FBA to the respiratory tract cells of said subject.

Preferably, the mammalian subject is a human subject.

While the method of the present invention is suitable for application to any suitable human subject, in a preferred embodiment, the method is used in a subject who is prone to, or is suffering from, a medical condition selected from the group consisting of: asthma, bronchospasm, bronchitis, bronchiolitis, and pneumonia.

In one aspect of the invention, the agent used to prevent and/or treat the infection is a composition comprising one or more peptides, wherein said peptide(s) have sequence homology to a portion of the human Flamingo homolog 1 cadherin molecule. The administration of this composition may also be used to treat an existing *S. pneumoniae* infection. The peptide for use in the present invention comprises at least five, and preferably at least ten amino acids, wherein said peptide has sequence identity of at least 60%, and preferably at least 90%, with a sub-domain of the human Flamingo homolog 1 protein (Swiss-Prot primary accession no. Q9NYQ7). The degree of sequence identity of two sequences is defined herein below.

Without wishing to be bound by theory, it is believed that the aforementioned peptides are able to exert their desired effect by means of binding to the FBA molecules present on the surface of the bacteria, thereby inhibiting the adhesion of said bacteria to the mucosal and other human cells lining the respiratory tract mucosal cells of the subject being treated.

In one preferred embodiment, the present invention is directed to a method of preventing and/or treating *S. pneumoniae* infection in mammalian subjects by means of administering to said subjects a composition comprising one or more peptides having sequence identity of at least 60% to the amino acid sequence spanning residues 2891-2903 of the member of the cadherin family known as human Flamingo homolog 1 (hFmi1) (Swiss-Prot primary accession no. Q9NYQ7; NCBI reference number gi:22095552). (This protein is also variously referred to as cadherin EGF LAG seven pass G-type receptor 3 precursor and CELR3_human.)

In another preferred embodiment, the aforementioned peptides have a sequence identity of at least 70% to the amino acid sequence spanning residues 2891-2903 of the member of the cadherin family known as human Flamingo homolog 1 (hFmi1) (Swiss-Prot primary accession no. Q9NYQ7).

In yet another preferred embodiment, the aforementioned peptides have a sequence identity of at least 90% to the amino acid sequence spanning residues 2891-2903 of the member of the cadherin family known as human Flamingo homolog 1 (hFmi1) (Swiss-Prot primary accession no. Q9NYQ7).

It is to be emphasized that the peptides used in the present invention (as defined hereinabove and hereinbelow) may comprise, in addition to amino acid sequences homologous to the hFmi1 sequence, flanking sequences of various lengths. Such flanking sequences may be sequences homologous to the native upstream and downstream sequences that flank residues 2891-2903 of the aforementioned hFmi1 sequences. Alternatively, the flanking sequences may be either modifications of said native flanking sequences or unrelated thereto.

In one preferred embodiment of this aspect of the invention, the aforementioned composition comprises one or more peptides selected from the group consisting of:

(SEQ ID NO 1)
a) Asp-Ser-Asp-Ser-Asp-Ser-Asp-Leu-Ser-Leu-Glu-Glu-Glu;

(SEQ ID NO 2)
b) Ala-Asp-Ser-Asp-Ser-Asp-Ser-Asp-Leu-Ser-Leu-Glu-Glu-Glu-Arg.

In one particularly preferred embodiment of this aspect of the invention, the aforementioned composition comprises a single peptide having the sequence:

(SEQ ID NO 2)
Ala-Asp-Ser-Asp-Ser-Asp-Ser-Asp-Leu-Ser-Leu-Glu-Glu-Glu-Arg

The peptide-containing compositions used in the above-defined method may be administered either systemically (e.g. by intramuscular or intravenous injection, or by oral administration) or locally (e.g. by inhalation). In a particularly preferred embodiment, the compositions are administered by nasal inhalation. The compositions, in this case, are preferably formulated either in the form of nasal drops or as a nasal spray. The compositions may also be formulated as creams, lotions, ointments or the like for topical administration the skin or mucosal membranes.

The present invention is also directed to the aforementioned peptide-containing pharmaceutical compositions themselves. In addition to the aforementioned active peptides, the compositions of the present invention may further comprise other pharmaceutically active agents including decongestants and antibiotic agents. Said compositions may also comprise bronchodilators, anti-inflammatory steroids, leukotriene antagonists, histamine receptor antagonists and other active pharmaceutical agents used to treat and/or prevent asthma and bronchospasm.

In another aspect, the present invention is directed to the use of one or more peptides as broadly defined above, and more specifically, peptides having sequence identity of at least 60% to the amino acid sequence spanning residues 2891-2903 of the member of the cadherin family known as human Flamingo homolog 1 (hFmi1) (Swiss-Prot primary accession no. Q9NYQ7), in the preparation of a medicament.

In one preferred embodiment, the aforementioned peptides have a sequence identity of at least 70% to the amino acid sequence spanning residues 2891-2903 of the member of the cadherin family known as human Flamingo homolog 1 (hFmi1) (Swiss-Prot primary accession no. Q9NYQ7).

In another preferred embodiment, the aforementioned peptides have a sequence identity of at least 90% to the amino acid sequence spanning residues 2891-2903 of the member of the cadherin family known as human Flamingo homolog 1 (hFmi1) (Swiss-Prot primary accession no. Q9NYQ7).

In addition, the above-defined peptides used in the preparation of a medicament may also comprise flanking sequences as defined hereinabove.

In a preferred embodiment the present invention is directed to the use of one or more peptides selected from the group consisting of:

(SEQ ID NO 1)
a) Asp-Ser-Asp-Ser-Asp-Ser-Asp-Leu-Ser-Leu-Glu-Glu-Glu;

(SEQ ID NO 2)
b) Ala-Asp-Ser-Asp-Ser-Asp-Ser-Asp-Leu-Ser-Leu-Glu-Glu-Glu-Arg;

in the preparation of a medicament.

In a particularly preferred embodiment, the peptide used to prepare the medicament is (SEQ ID NO 2)
Ala-Asp-Ser-Asp-Ser-Asp-Ser-Asp-Leu-Ser-Leu-Glu-Glu-Glu-Arg.

In one preferred embodiment, the aforementioned medicament is used to prevent infection of human subjects with S. pneumoniae. In another preferred embodiment, the medicament is used to treat a pre-existing S. pneumoniae infection.

The present invention also encompasses a method for vaccinating a human subject against infection with S. pneumoniae, wherein said method comprises inoculating the subject with a composition comprising one or more of the aforementioned peptides and one or more immunological adjuvants. Any suitable adjuvant having regulatory approval for use in human subjects may be used. One example of such a suitable adjuvant is alum.

The present invention also includes within its scope a vaccine composition comprising one or more of the aforementioned peptides together with one or more immunological adjuvants.

The invention is also directed to the use of one or more of the aforementioned peptides in the preparation of a vaccine composition. In one preferred embodiment, said vaccine composition is suitable for use in the prevention of disease and carrier states caused by S. pneumoniae.

In another aspect, the present invention is directed to an isolated peptide having sequence identity of at least 60% to the amino acid sequence spanning residues 2891-2903 of the member of the cadherin family known as human Flamingo homolog 1 (hFmi1) (Swiss-Prot primary accession no. Q9NYQ7).

In one preferred embodiment, the isolated peptide has sequence identity of at least 70% to the amino acid sequence spanning residues 2891-2903 of the member of the cadherin family known as human Flamingo homolog 1 (hFmi1) (Swiss-Prot primary accession no. Q9NYQ7).

In another preferred embodiment, the isolated peptide has sequence identity of at least 90% to the amino acid sequence spanning residues 2891-2903 of the member of the cadherin family known as human Flamingo homolog 1 (hFmi1) (Swiss-Prot primary accession no. Q9NYQ7).

In one preferred embodiment of this aspect of the invention, the isolated peptide has the following sequence:

(SEQ ID NO 1)
Asp-Ser-Asp-Ser-Asp-Ser-Asp-Leu-Ser-Leu-Glu-Glu-Glu.

In another preferred embodiment, the isolated peptide has the following sequence:

(SEQ ID NO 2)
Ala-Asp-Ser-Asp-Ser-Asp-Ser-Asp-Leu-Ser-Leu-Glu-Glu-Glu-Arg.

The present invention also encompasses a method for preventing and/or treating S. pneumoniae infection in mammalian subjects by means of administering to said subjects a composition comprising one or more agents selected from the group consisting of FBA, modified FBA, truncated FBA, FBA domain, subdomain or fragment, and a fusion protein comprising FBA or a modified or truncated form or domain, subdomain or fragment thereof.

In one preferred embodiment, the aforementioned composition comprises FBA. In one particularly preferred embodiment, the composition comprises recombinant FBA (rFBA).

In another preferred embodiment, the composition comprises a domain, subdomain, fragment, truncated form or chemically modified form of FBA.

The compositions used in the aforementioned method may be administered either systemically (e.g. by intramuscular or intravenous injection, or by oral administration in the form of capsules, tablets etc.) or topically (e.g. nasal spray, nasal drops, topical formulations for delivery via the skin or mucous membranes etc.). The compositions of the present invention may further comprise other pharmaceutically active agents including decongestants and antibiotic agents, bronchodilators, anti-inflammatory steroids, leukotriene antagonists, histamine receptor antagonists and other active pharmaceutical agents used to treat and/or prevent asthma and bronchospasm.

The present invention is also directed to the use of an agent selected from FBA, modified FBA, truncated FBA, FBA domains, subdomains or fragments, and fusion proteins comprising FBA or modified or truncated forms or domains, subdomains or fragments thereof in the preparation of a medicament. In one preferred embodiment, the invention provides the use of recombinant FBA in the preparation of a medicament.

In one preferred embodiment, the aforementioned medicament is used to prevent infection of human subjects with S. pneumoniae. In another preferred embodiment, the medicament is used to treat pre-existing S. pneumoniae infection.

The present invention further encompasses a method for preventing and/or treating S. pneumoniae infection in mammalian subjects by means of administering to said subjects a composition comprising antibodies directed against one or more epitopes present on the FBA molecule.

The compositions used in the aforementioned method may be administered either systemically (e.g. by intramuscular or intravenous injection, or by oral administration in the form of capsules, tablets etc.) or topically (e.g. nasal spray, nasal drops, topical formulations for delivery via the skin or mucous membranes etc.). The compositions of the present invention may further comprise other pharmaceutically active agents including decongestants and antibiotic agents, bronchodilators, anti-inflammatory steroids, leukotriene antagonists, histamine receptor antagonists and other active pharmaceutical agents used to treat and/or prevent asthma and bronchospasm.

The present invention is also directed to the use of anti-FBA antibodies in the preparation of a medicament.

In one preferred embodiment, the aforementioned medicament is used to prevent infection of human subjects with S. pneumoniae. In another preferred embodiment, the medicament is used to treat pre-existing S. pneumoniae infection.

The present invention also encompasses a method for treating sepsis caused by S. pneumoniae in mammalian subjects, wherein said method comprises administering to said subjects a composition comprising one or more peptides as hereinabove described.

The compositions mentioned above may include one or more pharmaceutically acceptable carriers and excipients.

All the above and other characteristics and advantages of the present invention will be further understood from the following illustrative and non-limitative examples of preferred embodiments thereof.

BRIEF DESCRIPTION OF THE DRAWINGS

FIG. 1 depicts the identification of the recombinant FBA-HAT fusion protein after electrophoretic separation. FIG. 1A shows a coomassie blue-stained 1D PAGE gel separation of a bacterial lysate, with the 33.5 kDa FBA-HAT band indicated by an arrow. FIGS. 1B and 1C, each show a single 33.5 kDa band on western blots after probing with anti-HAT and anti-rFBA antibodies, respectively.

FIG. 2 graphically depicts the dose-dependent inhibition of bacterial adhesion to A459 cells by 11 selected phages with the highest ability to bind rFBA. The inhibition due to each of said 11 phages is separately shown in FIGS. 2A to 2K, while

FIG. 3 graphically depicts the dose-dependent inhibition of the adhesion of encapsulated and non-encapsulated S. pneumoniae strains to A459 cells due to the addition of the 15 amino acid flamingo-related peptide.

FIG. 4 graphically illustrates the inhibitory effect of the flamingo-related peptide on S. pneumoniae colonization of the lungs and nasopharynx in mice following intranasal inoculation of S. pneumoniae cells that had been pre-incubated with the peptide.

FIG. 15 A records the level of bacterial load in the spleens, and FIG. 15 B records the percent of infected mice.

DETAILED DESCRIPTION OF PREFERRED EMBODIMENTS

Figure 2A:
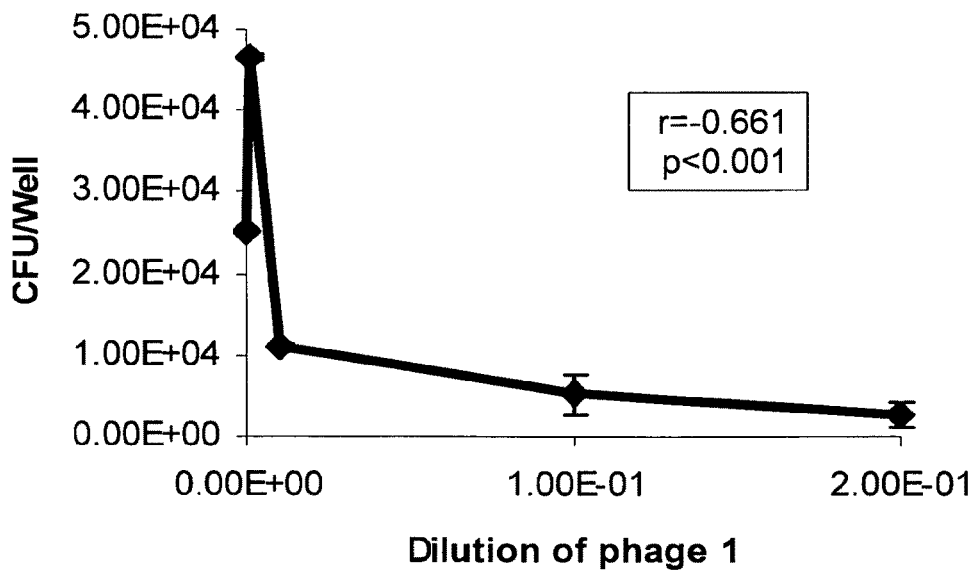
Figure 2B:
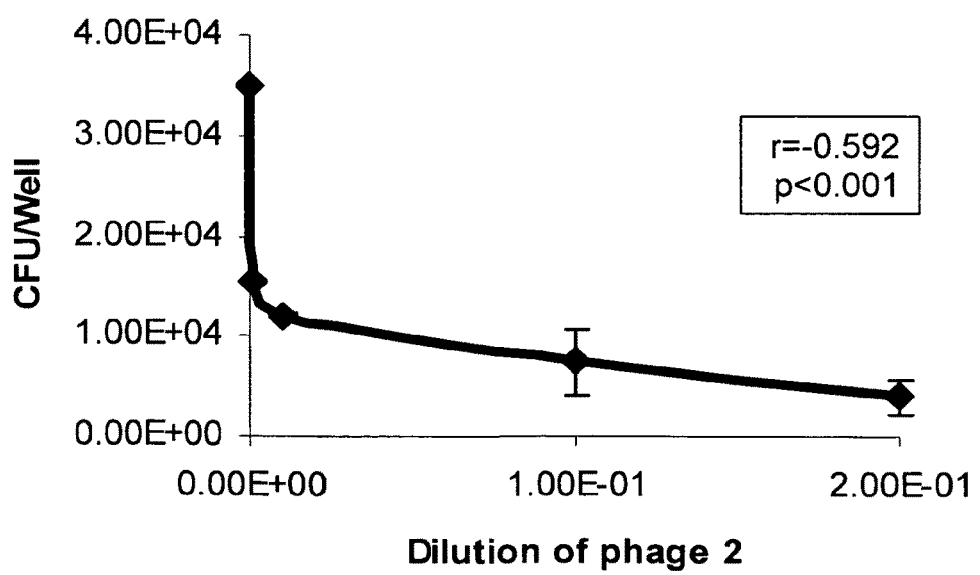
Figure 2C:
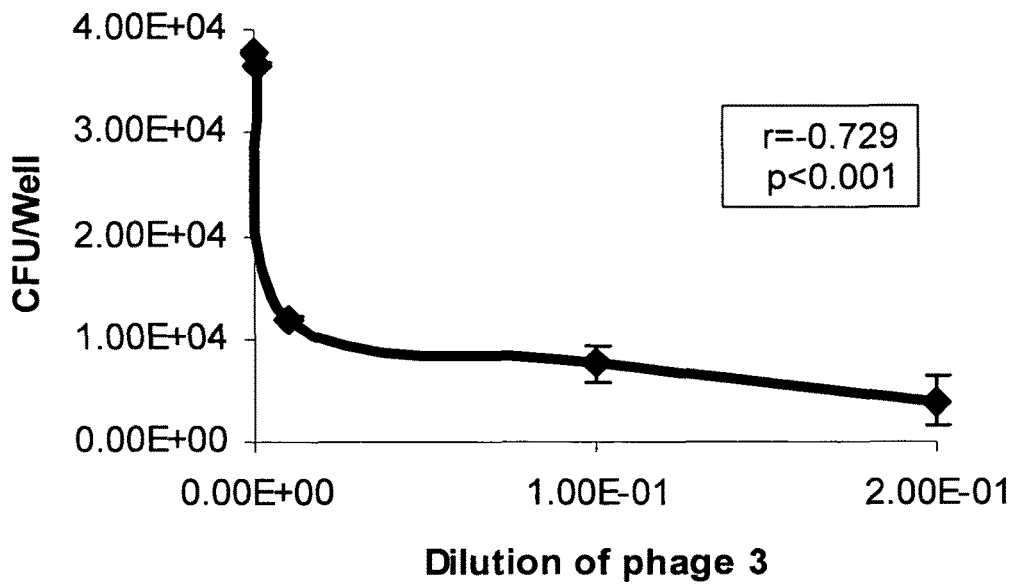
Figure 2D:
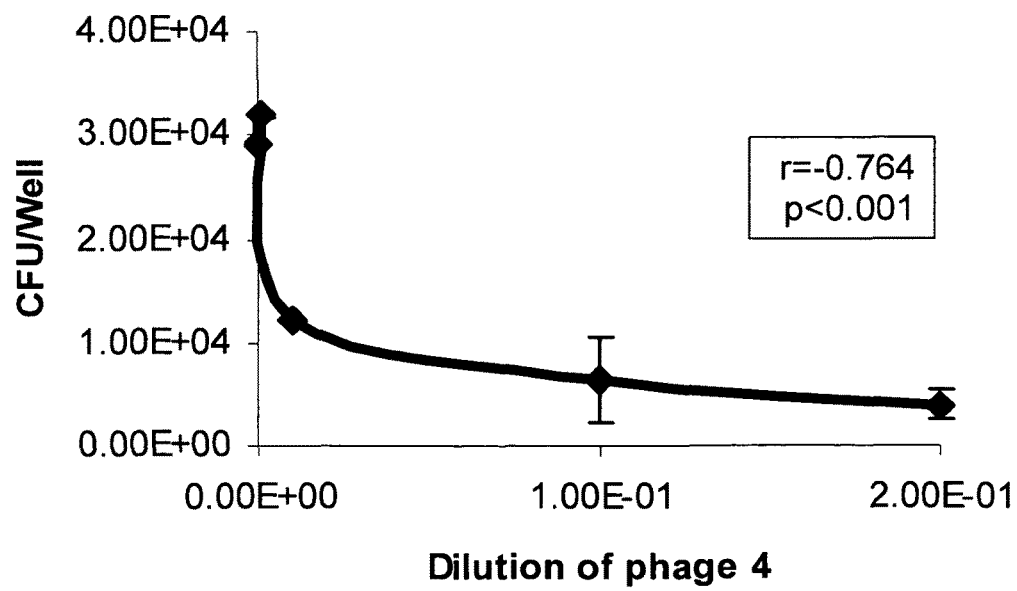
Figure 2E:
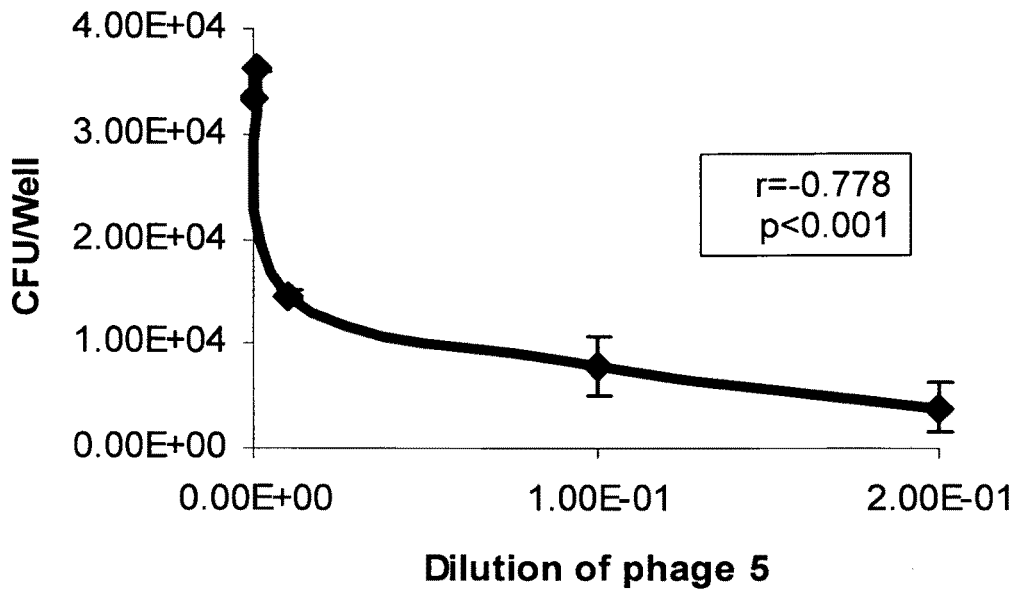
Figure 2F:
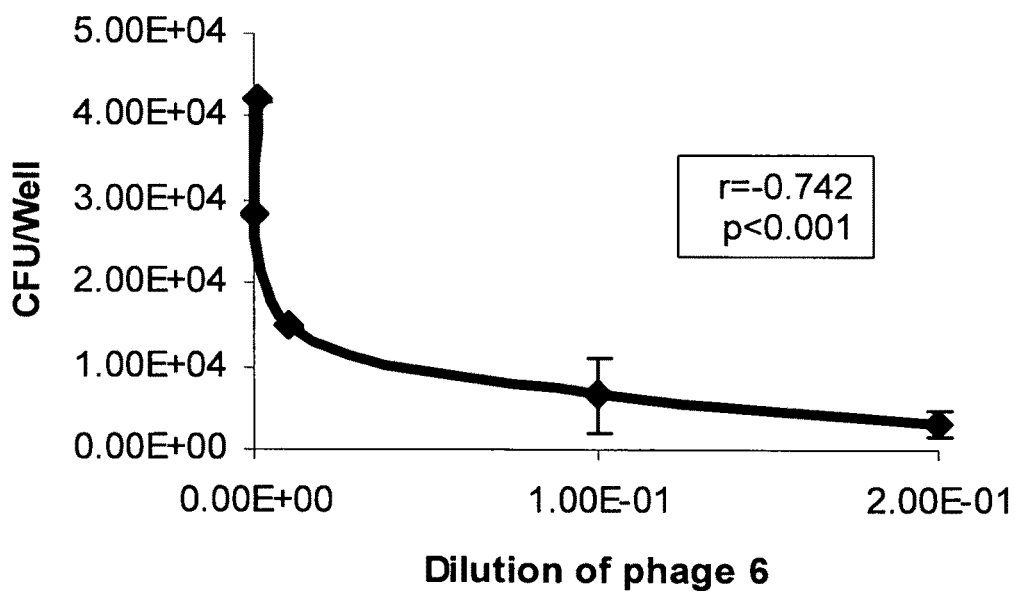
Figure 2G:
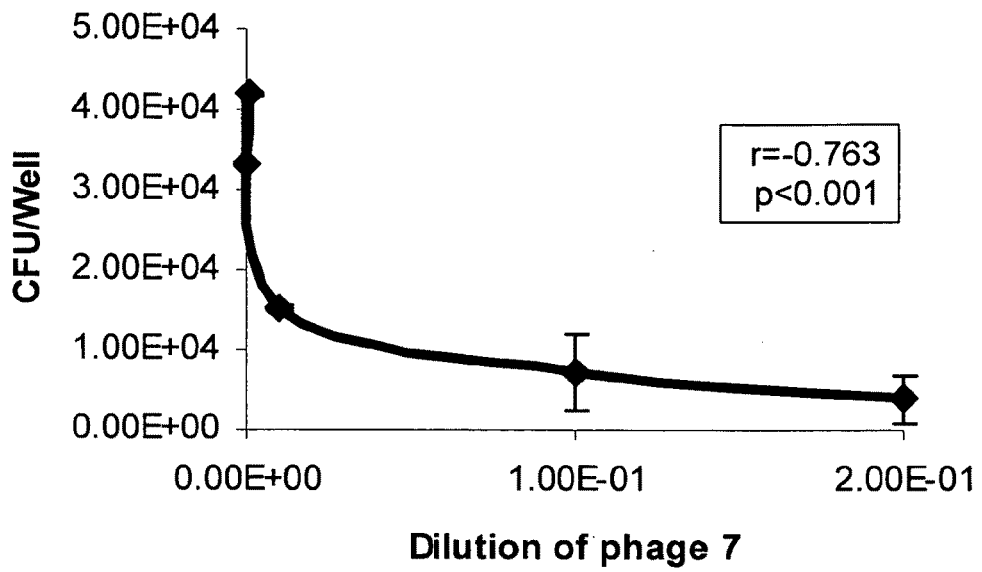
Figure 2H:
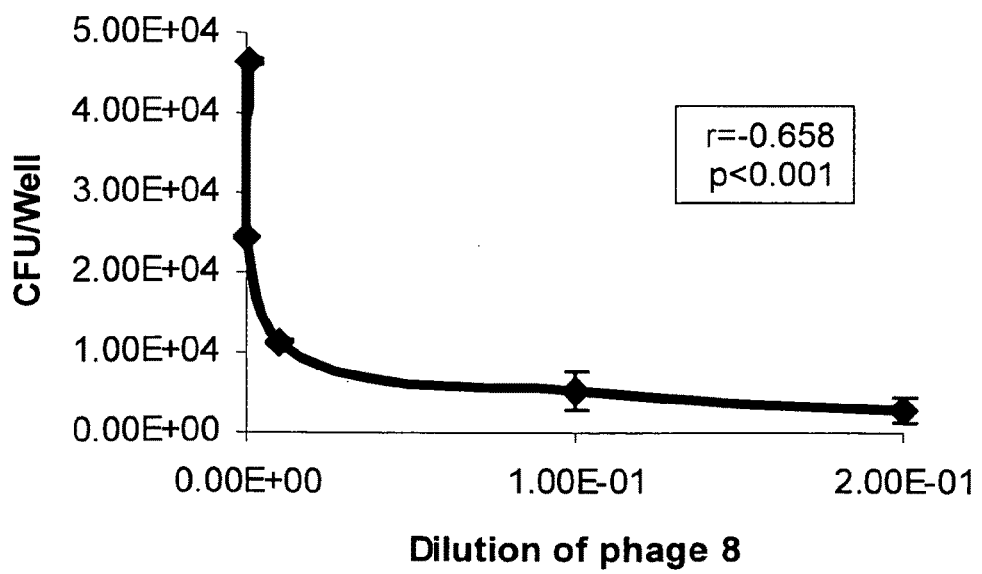
Figure 2I:
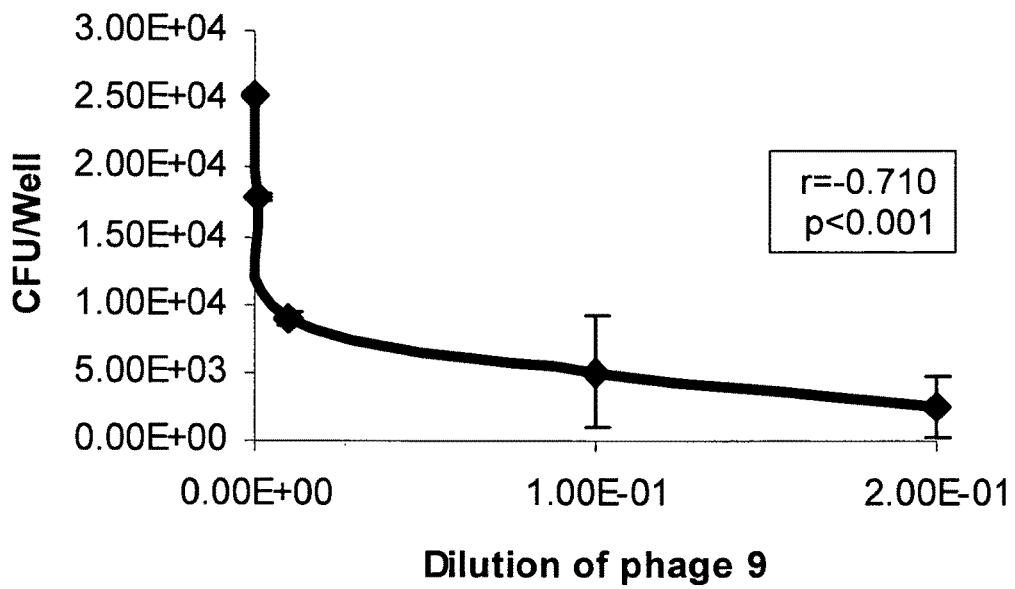
Figure 2J:
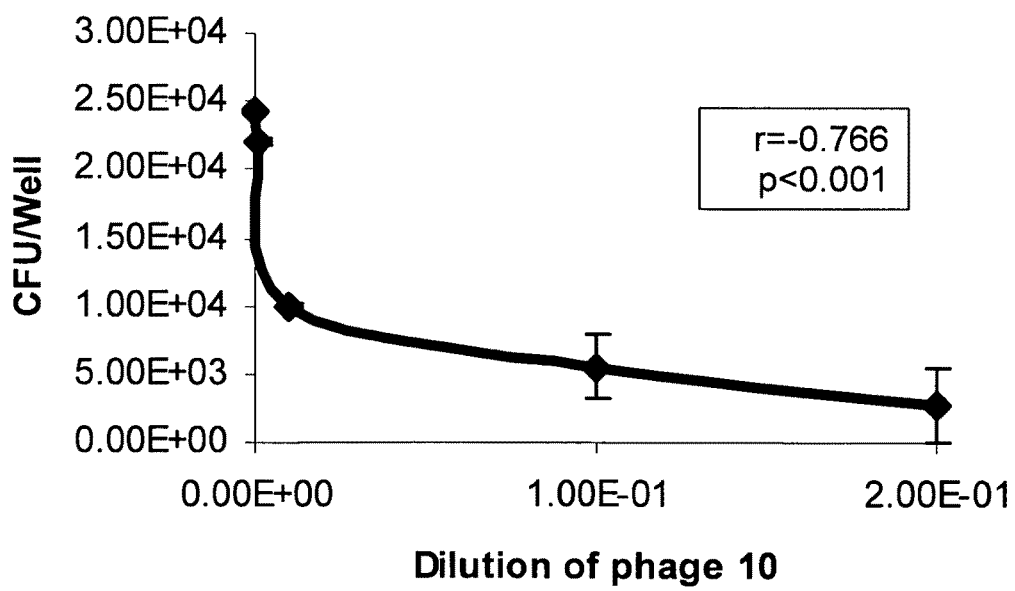
Figure 2K:
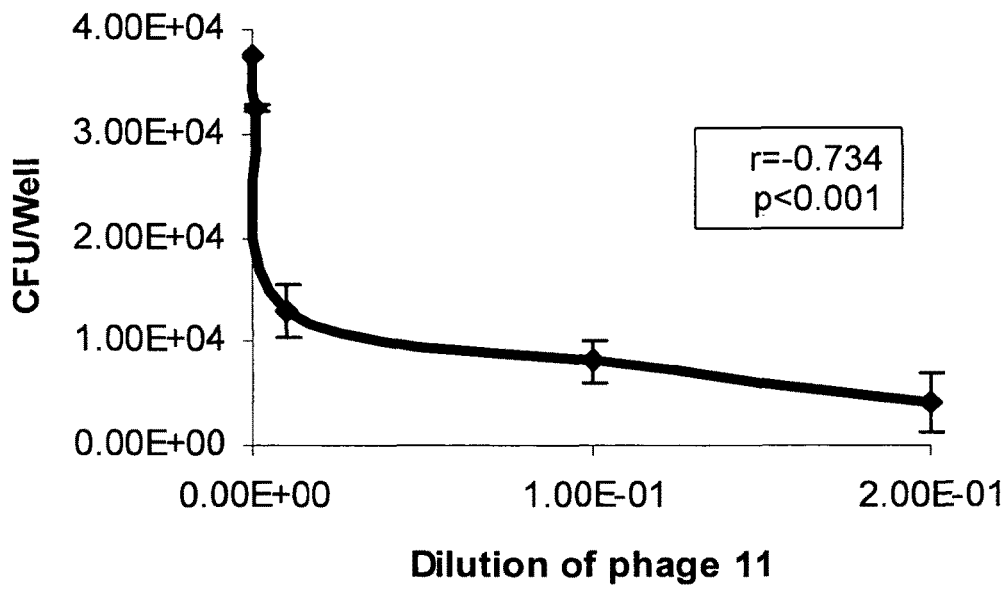

The inventors have unexpectedly found that certain peptides related to a sub-domain of the human flamingo cadherin molecule are capable of inhibiting the adhesion of S. pneumoniae to mammalian cells. It is to be noted that this subdomain (including the 13 amino acid sequence defined hereinabove as SEQ ID NO 1) is also present in other proteins, including the Anchor protein (SwissProt Accession No. Q5Y190), said Anchor protein having 78% identity to the Flamingo cadherin sequence. The present invention constitutes the various practical applications arising from this discovery, including, but not limited to the following:

1) The Flamingo Cadherin (FC) derived synthetic peptide may be used in S. pneumoniae preventive medicine:
   a. In many cases S. pneumoniae infection follows prior viral infection or allergic episodes. Inclusion of the FC peptide in nasal drops, nasal sprays, inhalations and creams directed to reduce congestion prevents the ensuing development of clinical S. pneumoniae diseases.
   b. One particular use of the FC peptide is in patients who are especially prone to S. pneumoniae infections (such as patients with asthma or with an immunocompromised immune system). Thus, inclusion of the FC peptide in the nasal drops, nasal sprays, inhalations, and creams directed to reduce congestion is used to prevent the developing of S. pneumoniae clinical disease.
2) Treatment with nasal drops, nasal sprays inhalation and creams to reduce bacterial spread and increase the therapeutic effectiveness of antibiotic treatments.
3) Systemic (for example oral or injected) application to prevent bacterial spread and the development of life threatening diseases that are caused by S. pneumoniae.

4) Usage of the peptide for immunization in the presence of adjuvant or conjugated to a carrier protein with adjuvant properties, with the aim of developing antibodies that might neutralize and prevent *S. pneumoniae* colonization and disease development.

The preferred peptides for use in the present invention are defined herein on the basis of their sequence homology to the amino acid sequence spanning residues 2891-2903 of the member of the cadherin family known as human Flamingo homolog 1 (hFmi1) (Swiss-Prot primary accession no. Q9NYQ7. The degree of sequence identity of two sequences may be defined, for the purpose of the present invention as follows:

$$\text{Sequence identity (\%)}=100\times(N_{total}-N_{diff})/N_{total},$$

Wherein $N_{total}$ is the total number of amino acid residues in one of the two peptide sequences being compared, and wherein $N_{diff}$ is the number of amino acid differences found between the two sequences when aligned.

The peptides for use in the present invention may be prepared by any suitable means. Generally, it is most convenient to chemically synthesize the peptide(s) having the desired sequence(s) by one of the several standard peptide synthesis techniques that are well known in the art.

The first peptide synthesis methods to find commercial use were liquid-phase techniques. While these techniques have largely been replaced by solid-phase methods, they still find use when large-scale industrial production of peptides is required.

In solid-phase peptide synthesis techniques (e.g. Merrifield, R. B., J. Am. Chem. Soc. 85. 2149-2154, 1963), peptide chains are constructed on linking groups that are immobilized onto inert beads. Following their synthesis, the desired peptide is removed from the beads by use of a non-specific cleavage agent such as trifluoroacetic acid. In order to ensure complete coupling during each round of amino acid addition, a large of excess of each amino acid is commonly used. In order to avoid problems of amino acid homopolymerization as a result of the aforementioned reagent excess, it is usual to incorporate protective groups (commonly either Fmoc or Boc) into the growing peptide chain. Prior to the subsequent amino acid addition, however, the protective group needs to be removed in a deprotection reaction step. Thus, in general outline, the solid-phase synthesis of a peptide involves repetition of the following steps:

Protective group is removed from trailing amino acids in a deprotection reaction Deprotection reagents washed away to provide clean coupling environment Protected amino acids dissolved in a solvent such as dimethylformamide (DMF) are combined with coupling reagents are pumped through the synthesis column in order to cause protection of the trailing amino acid residue Coupling reagents washed away to provide clean deprotection environment As an alternative to chemical synthetic methods, peptides may also be prepared by means of expression from recombinant DNA constructs in either prokaryotic or eukaryotic hosts (e.g. *E. coli* and yeasts, human cell lines etc.).

As a first stage, the location of the genes of interest may be determined by reference to a database such as the SwissProt database. The selected sequence may, where appropriate, be isolated directly by the use of appropriate restriction endonucleases, or more effectively by means of PCR amplification. Suitable techniques are described in, for example, U.S. Pat. Nos. 4,683,195, 4,683,202, 4,800,159, 4,965,188, as well as in Innis et al. eds., *PCR Protocols: A guide to method and applications.*

Following amplification and/or restriction endonuclease digestion, the desired gene or gene fragment is ligated either initially into a cloning vector, or directly into an expression vector that is appropriate for the chosen host cell type. In the case of the *S. pneumoniae* proteins, *Escherichia coli* is the most useful expression host. However, many other cell types may be also be usefully employed including other bacteria, yeast cells, insect cells and mammalian cell systems.

High-level expression of the desired protein or peptide within the host cell may be achieved in several different ways (depending on the chosen expression vector) including expression as a fusion protein (e.g. with factor Xa or thrombin), expression as a His-tagged protein, dual vector systems, expression systems leading to incorporation of the recombinant protein inside inclusion bodies etc. The recombinant protein will then need to be isolated from the cell membrane, interior, inclusion body or (in the case of secreted proteins) the culture medium, by one of the many methods known in the art.

All of the above recombinant DNA and protein purification techniques are well known to all skilled artisans in the field, the details of said techniques being described in many standard works including "Molecular cloning: a laboratory manual" by Sambrook, J., Fritsch, E. F. & Maniatis, T., Cold Spring Harbor, N.Y., $2^{nd}$ ed., 1989, which is incorporated herein by reference in its entirety.

The peptide-containing compositions used in the above-defined method may be administered to the intended subject either systemically (e.g. by intramuscular or intravenous injection or by oral administration in the form of tablets, capsules, syrups etc.) or locally (e.g. by inhalation). A therapeutically effective amount of the peptide will depend upon many factors including the age, weight and physical condition of the subject to be treated. Typical daily dose regime may be in the range between 0.02 mg/kg body to 50 mg/kg body.

In a particularly preferred embodiment, the compositions are administered by nasal inhalation. The compositions, in this case, are preferably formulated either in the form of nasal drops or as a nasal spray. The compositions may also be formulated as creams, lotions, ointments or the like for topical administration the skin or mucosal membranes.

As mentioned hereinabove, in a particularly preferred, the peptide-containing compositions are formulated as drops or a spray for administration by the nasal inhalation route. In one preferred embodiment, the nasal drops formulation comprises one or more peptides as defined hereinabove dissolved in a sterile 0.9% (w/v) sodium chloride solution. The solution may optionally contain preservatives such as 0.01% benzalkonium chloride, and/or other excipients. The total concentration of the peptide(s) in the solution will generally be in the range of 50-5000 μg/ml, more preferably 100-1000 μg/ml. In one preferred dosage regimen, one drop of the formulation is administered twice daily for three days. The formulation may also be administered with antibiotics or other pharmaceutical agents (as described hereinabove), either concurrently or consecutively. In the case of concurrent use, the additional pharmaceutical agent(s) may be formulated separately or may be included in the peptide-containing composition.

In a particularly preferred embodiment, the nasal drops formulation comprises a single peptide having the sequence:

(SEQ ID NO 2)
Ala-Asp-Ser-Asp-Ser-Asp-Ser-Asp-Leu-Ser-Leu-Glu-Glu-Glu-Arg.

Further details regarding the preparation and administration of different formulations containing the peptide compositions of the present invention may be found in standard reference works such as Remington's Pharmaceutical Sciences, Mack Publishing Co, Easton, Pa., USA (1980).

In another aspect of the present invention, the peptide-containing compositions defined hereinabove and claimed herein below may be used as vaccines, i.e. they are administered to a subject in such a form and manner that the immune system of said subject responds by producing specific antibodies to the peptide(s).

Generally, the peptides of the present invention are relatively short and therefore need to be administered together with an immunological adjuvant, in order to act as efficient immunogens.

Vaccines are generally, but not exclusively, administered by means of injection, generally by way of the intramuscular, intradermal or subcutaneous routes. Some vaccines may also be administered by the intravenous, intraperitoneal, nasal or oral routes.

The peptide containing preparations of the invention can be administered as either single or multiple doses of an effective amount of said protein. The term "effective amount" is used herein to indicate that the vaccine is administered in an amount sufficient to induce or boost a specific immune response, such that measurable amounts (or an increase in the measurable amounts) of one or more antibodies directed against the peptides used are detected in the serum or plasma of the vaccinated subject. The precise weight of peptide that constitutes an "effective amount" will depend upon many factors including the age, weight and physical condition of the subject to be vaccinated. The precise quantity also depends upon the capacity of the subject's immune system to produce antibodies, and the degree of protection desired. Effective dosages can be readily established by one of ordinary skill in the art through routine trials establishing dose response curves. Typical dose regime may be in the range between 0.02 mg/kg body to 50 mg/kg body.

The vaccines of the present invention will generally comprise an effective amount of one or more peptides as defined hereinabove as the active component, suspended in an appropriate vehicle. In the case of intranasal formulations, for example, said formulations may include vehicles that neither cause irritation to the nasal mucosa nor significantly disturb ciliary function. Diluents such as water, aqueous saline may also be added. The nasal formulations may also contain preservatives including, but not limited to, chlorobutanol and benzalkonium chloride. A surfactant may be present to enhance absorption of the subject proteins by the nasal mucosa.

However, in general, the vaccines of the present invention would normally be administered parenterally, by the intramuscular, intravenous, intradermal or subcutaneous routes, either by injection or by a rapid infusion method. Compositions for parenteral administration include sterile aqueous or non-aqueous solutions, suspensions, and emulsions.

Examples of non-aqueous solvents are propylene glycol, polyethylene glycol, vegetable oils such as olive oil, and injectable organic esters such as ethyl oleate. Besides the abovementioned inert diluents and solvents, the vaccine compositions of the invention can also include adjuvants, wetting agents, emulsifying and suspending agents, or sweetening, flavoring, or perfuming agents.

The aforementioned adjuvants are substances that can be used to non-specifically augment a specific immune response. Normally, the adjuvant and the composition are mixed prior to presentation to the immune system, or presented separately, but into the same site of the subject being vaccinated. Adjuvants that may be usefully employed in the preparation of vaccines include: oil adjuvants (for example, Freund's complete and incomplete adjuvants, which may be used in animal experiments only and which are forbidden for human use), mineral salts, alum, silica, kaolin, and carbon, polynucleotides and certain natural substances of microbial origin.

Further examples of materials and methods useful in the preparation of vaccine compositions are well known to those skilled in the art. In addition, further details may be gleaned from Remington's Pharmaceutical Sciences, Mack Publishing Co, Easton, Pa., USA (1980).

The following examples are provided for illustrative purposes and in order to more particularly explain and describe the present invention. The present invention, however, is not limited to the particular embodiments disclosed in the examples.

EXAMPLES

In the working Examples provided hereinbelow, the materials and methods used are as described in the following general 'Materials and Methods' section, unless otherwise stated.

Material and Methods

Reagents: Unless otherwise stated all chemicals and biochemicals of highest purity available were purchased from Sigma-Aldrich (St. Louis, Miss., USA).

Bacterial strains, growth conditions and growth medium: Four S. pneumoniae strains and two E. coli strains were used in this study. Two pairs of genetically unrelated encapsulated S. pneumoniae strains and their unencapsulated derivatives were used in this study as previously described (Mizrachi Nebenzahl Y. et al., FEMS Microbiology Let. 2004, 233:147-152). E. coli were grown in Luria-Bertani (LB) broth. Pneumococci were grown to mid logarithmic growth phase as determined by optical density (OD) in Todd-Hewitt broth (DIFCO Laboratories, Detroit, Mich., USA) supplemented by yeast extract (DIFCO Laboratories, Detroit, Mich., USA).

Bacterial growth and protein purification: Fructose-bisphosphate aldolase (FBA; SP0605 Streptococcus pneumoniae TIGR4) was cloned into the pHAT expression vector (BD Biosciences Clontech, Palo Alto, Calif., USA) as previously described (Backhed F, et al., J Biol Chem. 2002; 17:18198-205). Transformed E. coli host expression strain BL21(DE3)pLysS were grown overnight and expression of the recombinant his-tagged protein was induced by the addition of 1 mM IPTG to BL21(DE3)pLysS$^{+FBA}$ cells for 5 hours. The cells were harvested by centrifugation, and lysed in lysis buffer (8 M urea, 0.1 M NaH$_2$PO$_4$, 0.01 M Tris-Cl pH 8.0). The histidine-tagged recombinant proteins were purified using a Ni-NTA column (Qiagen GMBH, Hilden, Germany). The lysate containing rFBA was incubated with the Ni-NTA column for 1 hour at room temperature. Then the column was washed with wash buffer (8 M urea, 0.1 M NaH$_2$PO$_4$, 0.01 M Tris-Cl pH 6.3), and the recombinant proteins were recovered from the column using elution buffer (8 M urea, 0.1 M NaH$_2$PO$_4$, 0.01 M Tris-Cl, pH 5.9). Isolation of the proteins was confirmed by Western blot analysis using anti-HAT antibodies (BD Biosciences Clontech, Palo Alto, Calif., USA). The recombinant protein preparations were stored in elution buffer at −20° C.

Protein gel electrophoresis and staining: Sodium dodecyl sulfate polyacrylamide gel electrophoresis (SDS-PAGE) was performed using the Hoefer mini VE vertical electrophoresis system (Amersham Biosciences, San Francisco, Calif., USA). Where required, the proteins were then separated in the second dimension using 10% polyacrylamide gels. All gels were stained using Coomassie brilliant blue.

Western blot analysis: Protein mixtures were separated by SDS-polyacrylamide gel electrophoresis and transferred to nitrocellulose membranes (Bio-Rad Laboratories, Inc, Carlsbad, Calif., USA) as described elsewhere (Ling E et al., Clin. Exp. Immunol. 2004; 138:290-298). The immunological detection of immobilized proteins was performed as described before (ibid.).

Identification of proteins: Proteins spots were excised from the PAGE gel and washed with 150 μL of wash solution (50% methanol and 5% acetic acid) for 3 hours and dehydrated with 200 μL of acetonitrile (5 min.). Reduction and alkylation was performed with 30 μL of 10 mM DTT and 30 μL of 100 mM iodoacetamide. After rehydration with 200 μL of 100 mM ammonium bicarbonate (10 min.) gel pieces were dehydrated, completely dried in vacuum centrifuge and subjected to enzymatic cleavage (porcine trypsin; Promega) for 16 h at 37° C. in 50 mM ammonium bicarbonate buffer. Extraction of peptides was performed by adding 30 μL of 50 mM ammonium bicarbonate and 5% formic acid. Matrix-assisted laser desorption ionization-time of flight mass spectrometry (MALDI-TOF-MS) analysis was performed using the REFLEX III (Bruker-Daltonik, Bremen, Germany) mass spectrometer. Peptide peak lists were searched against the database of S. pneumoniae TIGR4 (www.matrixscience.com).

Recombinant protein production: Recombinant FBA (NP_345117) was expressed as previously described [Ling E, Feldman G, Portnoi M, et al. Glycolytic enzymes associated with the cell surface of Streptococcus pneumoniae are antigenic in humans and elicit protective immune responses in the mouse. Clin Exp Immunol 2004; 138:290-8] Pneumococcal immunogenic protein D (PsipD NP_346607) was expressed similarly using the following forward primer: GGATCCTTGAAAAAGAAGGAACTATC (SEQ ID NO:3) and reverse primer: GAATTCCAATTCTTCCTTG-TAGTCGT (SEQ ID NO:4). This protein is a S. pneumoniae cell wall derived protein not involved in bacterial adhesion to human cells and is being used as a control throughout. The protein is designated PsipD throughout the specification.

Recombinant Fructose Bisphosphate Aldolase (rFBA) Protein purification: Recombinant Fructose Bisphosphate Aldolase (FBA; SP0605 Streptococcus pneumoniae TIGR4) was purified from IPTG treated BL21(DE3)pLysS$^{+FBA}$ using the Ni-NTA columns as previously described (Backhed F, et al., J Biol Chem. 2002; 17:18198-205. The purified protein was separated by 1D PAGE (FIG. 1A) and the single band of 33.5 kDa, representing the FBA-HAT fusion protein identity, was analyzed and identity verified by MALDI-TOF analysis (Mascot score 146, Z score 2.43, sequence coverage 55%) demonstrating a 99% compatibility. The identity of the protein was further verified in western blots using Rabbit anti HAT antibodies (FIG. 1B) and anti rFBA antibodies produced in immunized mice (FIG. 1C). The identity and purity of the recombinant protein was verified for each preparation.

Immunization of mice with rFBA: Seven weeks old BALB/c female mice (Harlan Laboratories, Israel) were housed in sterile conditions under 12 hour light/dark cycles and fed Purina Chow and tap water ad libitum. Animal experimental protocols were reviewed and approved by the Institutional Animal Care and Use Committee of the Ben-Gurion University of the Negev, Beer Sheva, Israel. Mice were immunized intraperitoneally with 25 μg of rFBA and 75 μl of Inject Alum adjuvant (Pierce Biotechnology Inc, Rockford, Ill., USA) on days 0 (primary immunization) and 21 (booster). Control mice were sham immunized with adjuvant. Blood samples were collected from mice one week prior to immunization and one week after booster immunization. The sera were pooled for immunological assays.

Phage display library: The filamentous bacteriophages fd, which carry combinatorial random phage library, was kindly provided by Prof. J. Gershony (Tel Aviv, Israel) (Enshell-Seijffers D et al., Nucleic Acids Res. 2001 29 (10):E50-0).

50 μg rFBA in Tris buffered Saline (TBS) were added into 6 well plates (Corning, Inc. Corning, N.Y., USA) and incubated overnight at 4° C. Following blocking with 0.25% gelatin, TBS containing the phage library was added to the well and incubated overnight at 4° C. The unadhered phages were removed and the adhered phages were eluted with 0.1N HCL, 0.1% BSA in TBS pH 2.2 and neutralizing (6M Tris-HCL pH 9.1). The rFBA adhered phages, were grown in E. coli strain DH5α in Terrific broth and transferred to LB agar containing 100 μg/ml tetracycline for selection of phage carrying bacteria. Following incubation the plates were centrifuged to isolate the phages. The phages were precipitated with 50 μl poly ethylene glycol buffer (40 mM PEG, 3M NaCl), centrifuged for 40 minutes at 6000 g and resuspended in TBS.

To identify the nucleic acid sequence in positive (i.e. FBA-binding) phages, the DH5α E. coli carrying the phages were grown overnight at 37° C. in 5 ml LB broth. Following centrifugation the supernatant was removed and the DNA was recovered from the pellet using QIAprep spin M13 (Qiagene GmPh, Hilden, Germany). Sequencing was done by Daniel Biotec (Israel) using the primmer: 5' TTTCACGT-TGAAAATCTCC 3' (HyLabs, Rehovot, Israel; SEQ ID NO:5).

To verify the ability of the phages to bind rFBA, the phages were transferred to nitrocellulose membrane using a Dot Blot apparatus (Biometra, Gottingen, Germany), and treated sequentially with rFBA in 30 ml, mouse anti rFBA antibodies (1:5,000) and a secondary antibody (Peroxidase conjugated affinity pure goat anti mouse IgG; Jackson laboratories, West Groove, Pa., USA) in a western blot like assay. The results were obtained by exposing the membrane to films (AGFA, Geveart, Belgium).

Inhibition of S. pneumoniae adhesion to A549 cells by addition of phages: A549 cells (type II epithelial lung carcinoma cells; ATCC, Rockville, Md., USA) were grown in DMEM medium supplemented with 10% foetal calf serum with penicillin and streptomycin (100 μg/ml each) at 37° C. in a humidified incubator. A549 cells ($2.5 \times 10^4$/well) were cultured on fibronectin coated plates, to increase A549 cell adhesion to the wells and prevent their detachment during washings, in the absence of antibiotic for 24 hours at which time the cells reached confluence ($5 \times 10^4$ cells/well on average). The plates were blocked with 1% gelatine for 1 hour and $10^6$ CFU bacteria were added per well. The adhesion of S. pneumoniae to uncoated plates was negligible (<80 CFU/ml). The number of bacteria that adhered to fibronectin coated plates (8000±100 SD CFU/ml on average) was subtracted afterwards to determine the net number of bacteria that adhered to the A549 cells only. rFBA at the denoted concentrations (ranging from 5-30 μg/ml) was added to the cultured cells and incubated for an hour. Following extensive washings *S. pneumoniae* (10⁶ CFU) were added for 1 hour incubation. To identify phages able to interfere in bacterial adhesion the bacteria were preincubated with the phages for 1 hour centrifuged and added to the cultured cells. Viability of the bacteria was tested prior to and after the incubation with the phages. Following 1 hour incubation, the wells were extensively washed (×5), for the removal of non adherent bacteria. The A549 cells were liberated by 0.25% trypsin-EDTA for 5 minutes at 37° C. and plated, in serial dilutions, onto Blood agar plates. The Blood agar plates were incubated for 18 hours at 37° C. The experiments were performed in triplicates and repeated three times on different occasions.

Inhibition of *S. pneumoniae* nasal and lung colonization with flamingo cadherin-related peptide: Seven weeks old BALB/c female mice (Harlan Laboratories, Israel) were housed in sterile conditions under 12 hour light/dark cycles and fed Purina Chow and tap water ad libitum. Animal experimental protocols were reviewed and approved by the Institutional Animal Care and Use Committee of the Ben-Gurion University of the Negev, Beer Sheva, Israel. For respiratory challenge with virulent *S. pneumoniae* mice were anaesthetized with Isoflurane ($R_x$Elite, Meridian, Id., USA) and inoculated intranasally (i.n.) with the denoted colony forming units (CFU) bacteria (in 25 µl PBS) prior and after treatment with the flamingo cadherin derived peptide at the denoted concentrations. At 3, 6, 24 and 48 hours following inoculation the nasopharynx and the lung were excised, homogenized and plated onto blood agar plates. The experiments were performed with groups of 4 mice at each treatment and each time point and the experiments were repeated on three different occasions.

Inhibition of *S. pneumoniae* adhesion to A549 cells following addition of rFBA: A549 cells (type II epithelial lung carcinoma cells; ATCC, Rockville, Md., USA) were grown in DMEM medium supplemented with 10% foetal calf serum with penicillin and streptomycin (100 µg/ml each) at 37° C. in a humidified incubator. A549 cells (2.5×10⁴/well) were cultured on fibronectin coated plates, to increase A549 cell adhesion to the wells and prevent their detachment during washings, in the absence of antibiotic for 24 hours at which time the cells reached confluence (5×10⁴ cells/well on average). The plates were blocked with 1% gelatine for 1 hour and 10⁶ CFU bacteria were added per well. The adhesion of *S. pneumoniae* to uncoated plates was negligible (<80 CFU/ml). The number of bacteria that adhered to fibronectin coated plates (8000±100 SD CFU/ml on average) was subtracted afterwards to determine the net number of bacteria that adhered to the A549 cells only. rFBA at the denoted concentrations (ranging from 5-30 µg/ml) were added to the cultured cells and incubated for an hour. Following extensive washings *S. pneumoniae* (10⁶ CFU) were added for 1 hour incubation. To identify phages able to interfere in bacterial adhesion the bacteria were preincubated with the phages for 1 hour centrifuged and added to the cultured cells. Viability of the bacteria was tested prior and after the incubation with the phages. Following 1 hour incubation, the wells were extensively washed (×5), for the removal of non adherent bacteria. The A549 cells were liberated by 0.25% trypsin-EDTA for 5 minutes at 37° C. and plated, in serial dilutions, onto Blood agar plates. The Blood agar plates were incubated for 18 hours at 37° C. The experiments were performed in triplicates and repeated three times on different occasions.

Inhibition of encapsulated *S. pneumoniae* to A549 lung carcinoma cells with anti rFBA antibodies: Bacteria were treated at the denoted concentrations with anti-rFBA serum for 30 minutes centrifuged and added to the cultured A549 cells for 60 minutes incubation. Excess bacteria were removed and the cells detached with trypsin and plated onto Blood agar plates. The experiments were performed in triplicates and repeated on three different occasions.

Immunization of mice with rFBA and PsipD: Seven week old BALB/cOlaHsd (BALB/c) female mice (Harlan Laboratories, Israel) were immunized intraperitoneally with 25 µg of rFBA [Ling et al., supra] or 25 µg of PsipD or 25 µg of Flamingo Cadherin receptor derived synthetic peptide (FCRP) fused to keyhole limpet hemocyanin (KLH; Sigma-Aldrich, Ltd. Rehovot, Israel) with Inject Alum adjuvant (Pierce Biotechnology Inc, Rockford, Ill., USA) at days 0 and 21. Blood samples were collected prior to and one week after booster immunization. All animal experimental protocols were reviewed and approved by the Institutional Animal Care and Use Committee of the Ben Gurion University of the Negev, Beer Sheva, Israel.

Immunization of rabbits: Three month old albino rabbits were immunized with 200 µg rFBA or 200 µg FCRP-KLH fusion protein in complete Freund's adjuvant subcutaneously and intramuscularly. Booster immunizations were performed with incomplete Freund's adjuvant.

Flow cytometry and antibodies: A549 cells were incubated with mouse anti-FCRP-KLH serum, mouse anti-PsipD serum or control mouse serum, washed and stained with FITC-conjugated-F(ab')₂-Goat-anti-mouse-IgG+IgM (Jackson ImmunoResearch, West Grove, Pa.). Flow cytometry was performed using a FACSCalibur flow cytometer (Becton Dickinson, Mountain View, Calif.). Data files were acquired and analyzed using BD CELLQuest™ 3.3 software.

Western blots: rFBA and FCRP were separated by 1D-SDS PAGE, transferred to nitrocellulose and probed with FCRP or rFBA, respectively. Rabbit anti-FCRP-KLH serum or rabbit anti rFBA was added respectively. In both cases, anti-rabbit IgG (Jackson ImmunoResearch, West Grove, Pa.) was used for final identification. In the control experiment preimmune serum was used as first antibody.

Bioinformatic analysis: The nucleic acid sequences of the inserted peptides in the positive phages were aligned against the human genome in the NCBI database using the Blast software. Prediction of membrane-spanning regions and their orientation was done using TMHMM server v 2.0.

Statistical analysis: The Spearman regression analysis was used to verify the ability of phages and peptides to inhibit bacterial adhesion to A549 lung epithelial cells in a concentration dependent manner. Further verification was done using the two-way ANOVA for repeated measurements.

Example 1

Identification of Biologically Active rFBA Binding Phages

In order to identify rFBA binding phages a random phage display library (FMC12C) was screened by the panning method, as described hereinabove. The rFBA binding phages were grown and retested for their ability to bind rFBA using a western blot like assay. Using this screening method some phages, including the phage without insert, were found not to bind rFBA, others were partially positive and 30 phages, which displayed the highest ability to bind rFBA were selected for further studies.

Figure 2L:
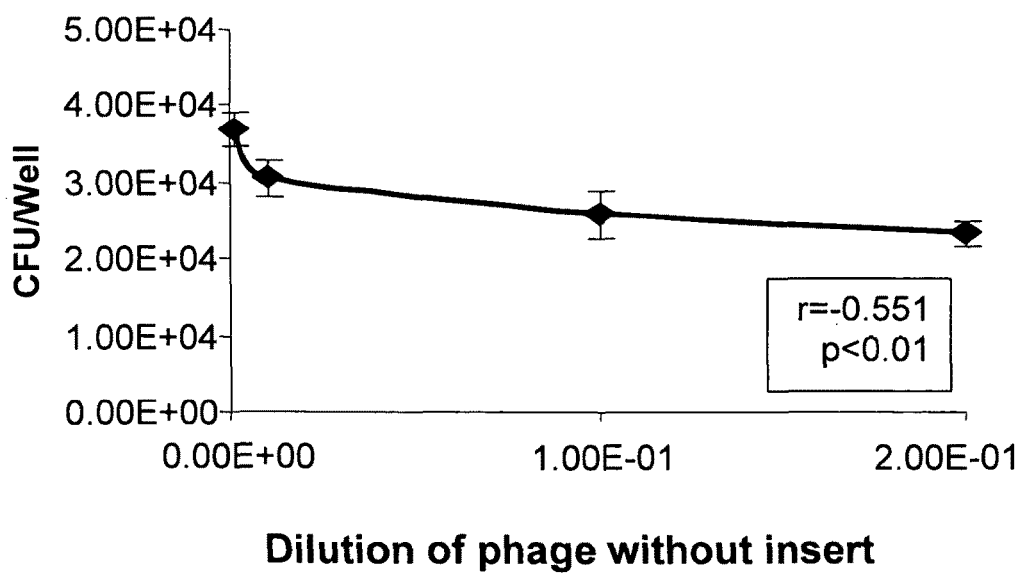
FIG. 2L depicts the effect of a phage lacking an insert (also exemplifying the negative phages).

The 30 phages that bound rFBA were amplified in DHα *E. coli* and tested for their ability to interfere in *S. pneumoniae* adhesion to A549 lung derived cells. Unencapsulated *S. pneumoniae* serotype 3 strain 3.8DW bacteria were incubated with the selected phages using the denoted dilutions prior to their addition to the A549 cells. Eleven out of the 30 phages demonstrated a significant inhibition of unencapsulated *S. pneumoniae* serotype 3 strain 3.8DW adhesion to the cultured A549 cells starting at 1:10000 (10⁸ phages/ml) dilution ($p<0.001$) and reached 86%-96% inhibition at 1:10 dilution ($10^{11}$ phages/ml) of the phages. These 11 phages inhibited bacterial adhesion in a dose dependent manner (r≤−0.778, p<0.001; FIG. 2A-K). The negative phages and the phage lacking a peptide insert inhibit only 20% of *S. pneumoniae* adhesion to the A549 cells (exemplified by phage without insert; FIG. 2L). Although this inhibition was significant, the extent of inhibition by these phages was significantly lower (p<0.001) than the inhibitory activity of the 11 positive phages.

Example 2

Identification of FBA Target Protein

To identify FBA target protein, the peptide-inserts in the envelope protein of the 11 phages found to be capable of interfering with *S. pneumoniae* adhesion to the cultured epithelial cells were amplified and sequenced. The nucleotide sequences were translated into the corresponding amino acid sequences as shown in the following table:

TABLE I

| Inhibitory sequence | Phage number |
|---|---|
| Gly Asp Val Glu Asp Phe Gly Gly Asp | 1 |
| Glu Glu stop codon | 2 |
| Glu Glu Tyr Ala Asp | 3 |
| Asp Glu Glu Gly Cys Asp Cys Tyr | 4 |
| Ser Tyr Glu Glu Ser | 5 |
| Asp Glu Gly | 6 |
| Asp Ser Ser Asp Cys Asp Leu Ala Trp Glu Glu Glu | 7 |
| Gly Gly Gly Ala Trp Glu Ser Asp Trp Glu Ser Asp | 8 |
| Ser Glu Ser Glu | 9 |
| Asp Ser Tyr Gly Ser | 10 |
| Gly Gly Ala Glu | 11 |

All the sequences were combined and aligned against the human genome in the NCBI data base using the BLAST software. Two membrane proteins were identified, each containing peptides homologous to the phage derived peptide sequences: the Flamingo cadherin protein and the opioid receptor protein.

gi|22095552|sp|Q9NYQ7|CLR3 HUMAN
Cadherin EGF LAG Seven-Pass G-Type Receptor 3 Precursor
(Flamingo homolog 1) (hFmi1) (Multiple epidermal growth factor-like domains 2) (Epidermal growth factor-like 1)
Length=3312
Score=23.5 bits (48), Expect=249
Identities=9/13 (69%), Positives=10/13 (76%), Gaps=1/13 (7%)
Query: 1 DS-SDCDLAWEEE 12
       DS SD DL+ EEE
Sbjct: 2891 DSDSDSDLSLEEE 2903

Using the TMHMM software the homologous areas in the Flamingo cadherin and the opioid receptor were analyzed. The area of homology to the FBA binding peptides were found to reside in the extracellular domain of Flamingo cadherin, with a 69% homology. However, the area of homology to the opioid growth factor receptor appears at the N-terminal intracellular domain with only 45% homology to the FBA binding peptides.

The homologous area in the Flamingo-Cadherin (FC) protein to the FBA binding peptides was found between amino acids 2891-2903.

Alignment analysis using the RELIC software revealed that 9 out of the 11 peptide sequences from the positive phages matched different regions of FCR (Table II). The insert peptide in phage number 7 aligned to FCR in three different areas with the highest homology.

TABLE II

Homology of peptide inserts to Flamingo Cadherin Receptor.

| Phage number | insert sequence | Homology to Cadherin |
|---|---|---|
| 1 | GDVEDFGGD | GDVEDFGGD<br>$^{28}$LSQEELGGG$^{36}$ |
| 3 | EEYAD | EEYAD<br>$^{2298}$EEYA$^{2302}$ |
| 5 | SYEES | SYEES<br>$^{2812}$LFEES$^{2816}$ |
| 6 | DEG | DEG<br>$^{1095}$DEG$^{1097}$ |
| 7 | DSSDCDLAWEEE | DSSDCDLAWEEE<br>$^{1466}$TGEDCELDTEAG$^{1478}$<br>DSSDCDLAWEEE<br>$^{1629}$SVDDCDVAVALQ$^{1641}$<br>DS-SDCDLAWEEE<br>$^{2891}$DSDSDSDLSLEEE$^{2903}$ |
| 8 | GGGAWESDWESD | GGGAWESDWESD<br>$^{57}$GGGALALCPESS$^{68}$ |
| 9 | SESE | SESE<br>$^{2911}$SESE$^{2914}$ |
| 10 | DSYGS | DSYGS<br>$^{2666}$EGYGN$^{2670}$ |
| 11 | GGAE | GGAE<br>$^{1617}$GGAQ$^{1620}$ |

Example 3

Synthesis of 15 Amino Acid FC-Derived Peptide

A 15 amino acid peptide from Flamingo-cadherin, based on the 13 residue homologous area described in Example 2, with two additional flanking amino acids (one N-terminal and one C-terminal, both present in the native FC sequence), was synthesized using the Sigma Genosys peptide synthesis service (Sigma Chemical Co., St. Louis, Mo.).

According to the technical protocols provided by Sigma, the peptide synthesis technique used is based on the use of FMOC chemistry under continuous flow conditions using PEG-Polystyrene resins. Peptides are synthesized in a C terminus-to-N terminus direction, following which they are removed from said resin and de-protected using a TFA/DTT/H2O/Triisopropyl silane (88/5/5/2) cleavage cocktail. Peptides are then precipitated from the cleavage cocktail using cold diethyl ether. The precipitate is then washed three times with the cold ether and then dissolved in a buffer solution containing $H_2O$/ACN/HOAC (75/20/5). Finally, the washed peptides are lyophilized from the aforementioned buffer solution. The purity of the synthesized peptides is assessed using reversed phase chromatography on a Supelco Bio Wide Pore column, and by MALDI-TOF mass spectrometry, and if required, further purification of the peptide is performed by reversed phase chromatography.

The sequence of the 15 amino acid residue peptide synthesized using the above method is:

```
                                              (SEQ ID NO: 2)
H-Ala-Asp-Ser-Asp-Ser-Asp-Ser-Asp-Leu-Ser-Leu-Glu-
Glu-Glu-Arg-OH.
```

Figure 7A:
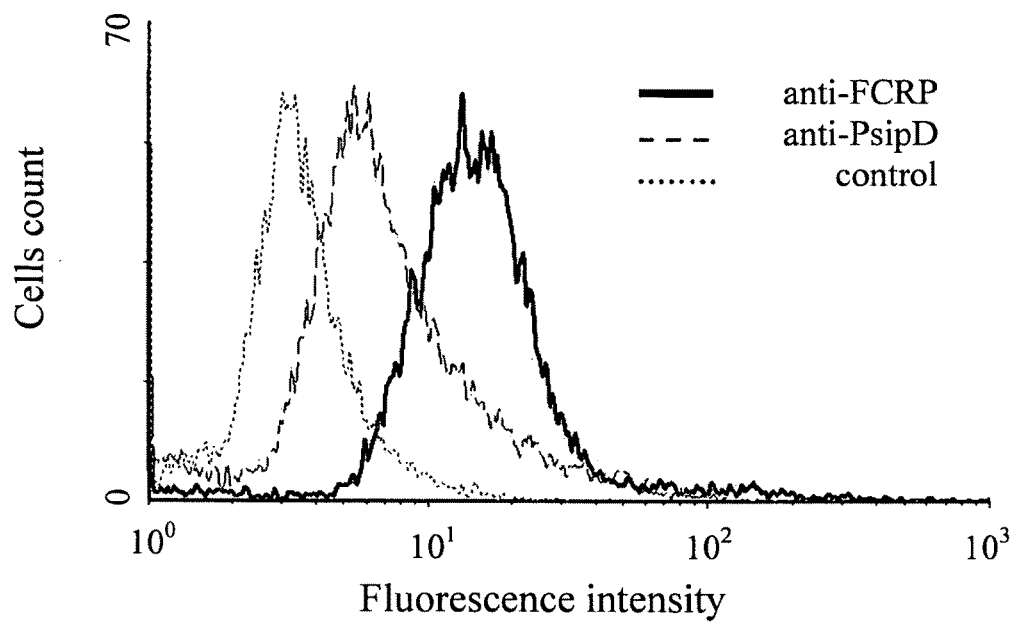
FIG. 7 shows the results of experiments performed in order to confirm the localization of FCR on the surface of A549 cells and the direct binding of rFBA to FCRP. A549 cell were stained with rabbit anti FCRP followed by FITC labelled anti rabbit IgG and analysed by flow cytometry (FIG. 7A). Anti PsipD antiserum and anti KLH antiserum (FIG. 7B) were used as controls. Western blots were performed to SDS PAGE resolved rFBA that was transferred to nitrocellulose and probed sequentially with FCRP, rabbit anti FCRP and HRP labelled anti rabbit IgG (FIG. 7C) No labelling of rFBA could be observed when FCRP was omitted. Conversely, FCRP was separated on SDS PAGE transferred to nitrocellulose and probed sequentially with rFBA, rabbit anti rFBA antiserum and HRP labelled anti rabbit IgG (FIG. 7D). No labelling of FCRP could be observed when rFBA was omitted.
Figure 7B:
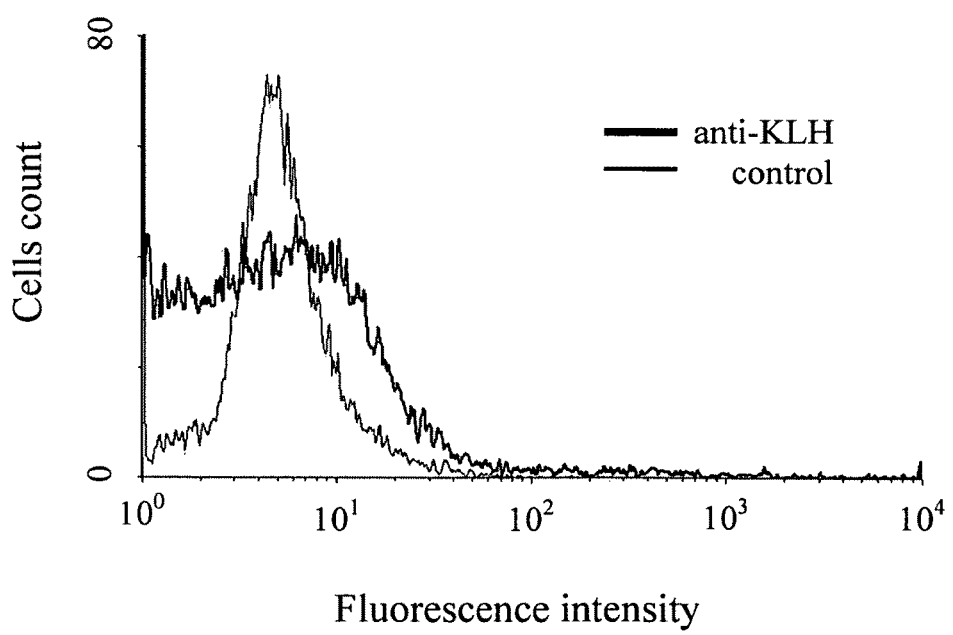

Localization of FCR on the surface of A549 cells was verified by flow cytometry using mouse anti-FCRP-KLH serum followed by goat anti mouse IgM+IgG FITC. The majority (92%) of A549 cells are stained positively by anti-FCRP-KLH serum, whereas the cells are not stained by the pre-immune serum, by another control serum (anti-PsipD serum; FIG. 7A) or by anti-KLH antibodies (FIG. 7B).

To determine more directly whether FCRP binds to rFBA, Western blot like assays were performed where rFBA is separated using 1D SDS-PAGE, transferred to a nitrocellulose membrane and probed with FCRP. Binding of FCRP was detected by incubating the membrane sequentially with rabbit anti-FCRP-KLH serum and anti-rabbit IgG. Using this protocol, a band of 33.5 kDa was shown to bind FCRP, corresponding to the molecular weight of the rFBA-HAT fusion protein (FIG. 7C). In the control (FIG. 7D) the first antibody was a pre-immune serum. In the converse experiment, when FCRP is separated on SDS-PAGE, a band of approximately 1.5 kDa corresponding to the molecular weight of FCRP is bound by rFBA (FIG. 7 E). In the control (FIG. 7F) the first antibody was a pre-immune serum.

Example 4

The Biological Activity of the Flamingo Cadherin (FC) Derived Peptide In Vitro

Figure 3A:
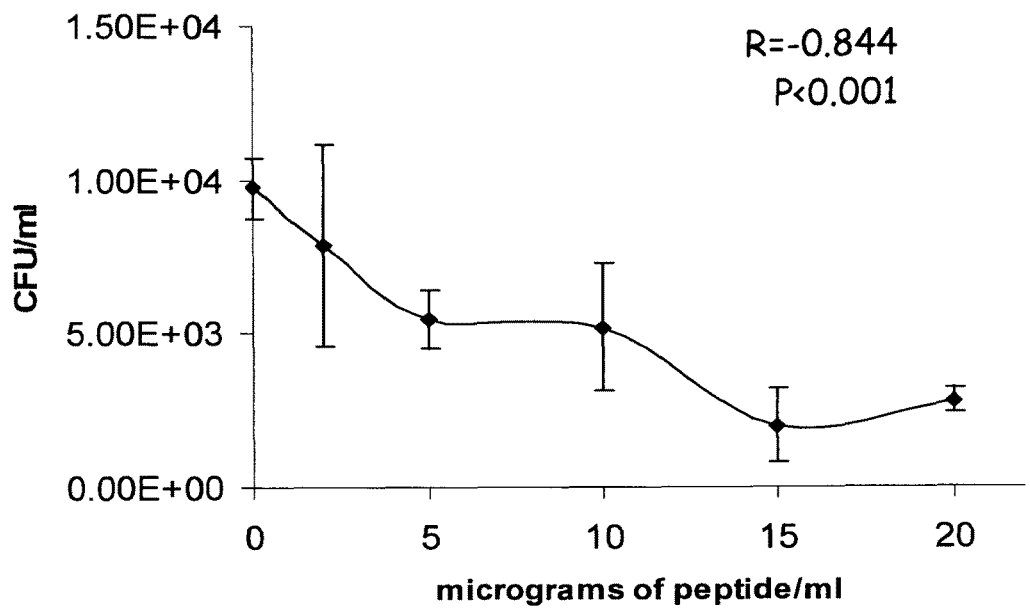
FIGS. 3A to D present, respectively, the adhesion inhibition data for S. pneumoniae encapsulated serotype 3 strains WU2, unencapsulated serotype 3 strain 3.8DW, encapsulated serotype 2 strain D39 and unencapsulated serotype 2 strain R6.
Figure 3B:
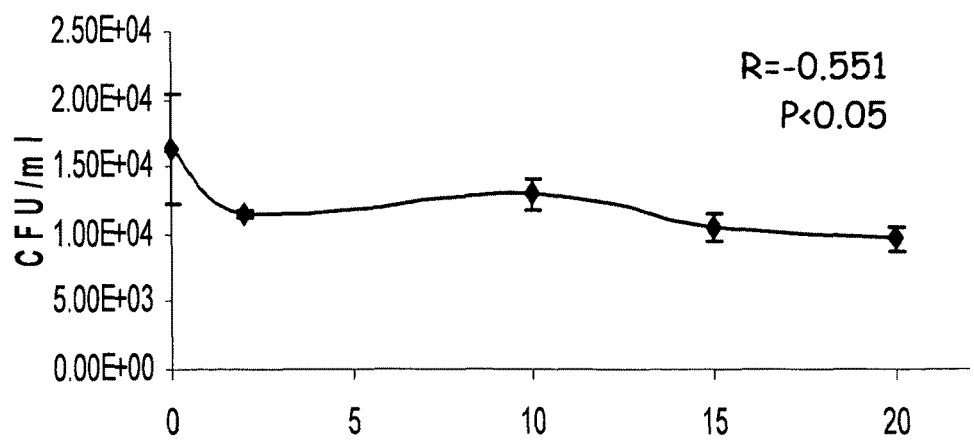
Figure 3C:
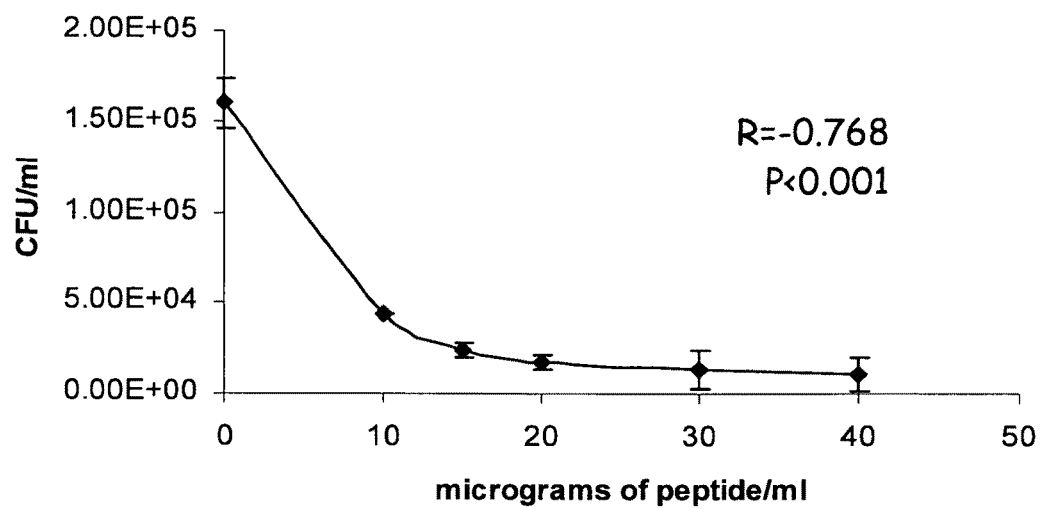
Figure 3D:
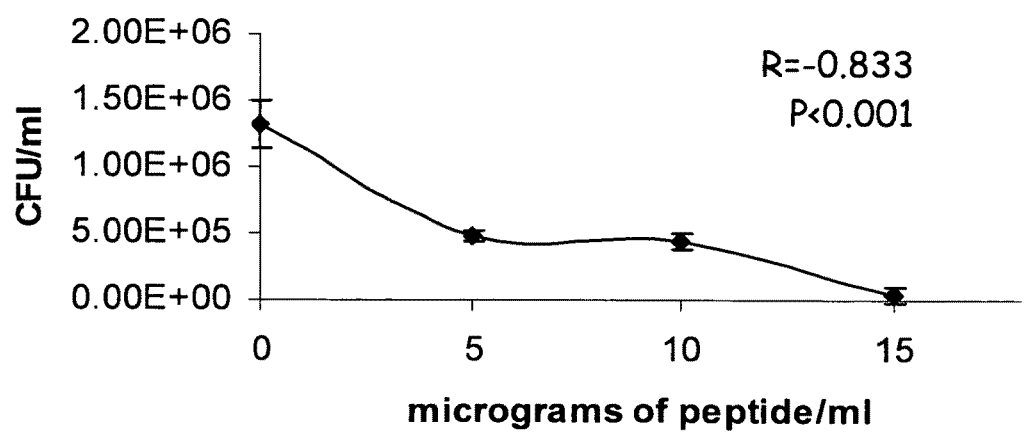

The ability of FC derived synthetic peptide to interfere in S. pneumoniae adhesion to A459 cells was analyzed. FC peptide ability to interfere in S. pneumoniae adhesion to A549 cells of encapsulated S. pneumoniae serotype 3 strain WU2 and serotype 2 strain D39 and their unencapsulated derivatives 3.8DW and R6, respectively was tested. FC inhibited significantly in a dose dependent manner ($r=-0.844$, $p<0.001$) the adhesion of the S. pneumoniae strain WU2 to A549 cells. Maximal adhesion was achieved at 15 µg/well FC peptide (80%; FIG. 3A). Inhibition of the non-encapsulated mutant strain 3.8DW was dose dependent ($r=-0.551$, $p<0.05$; FIG. 3B) and reached maximal adhesion inhibition of 41% with 20 µg/well of FC derived peptide. Furthermore, the peptide inhibited both the D39 and the R6 strains adhesion to A549 significantly ($p<0.001$) at 5 µg/well. In both strains, the inhibition of bacterial adhesion was concentration dependent ($r=-0.768$, $p<0.001$; $r=-0.833$, $p=0.001$, respectively; FIGS. 3C and 3D). FC peptide inhibited 90% of S. pneumoniae strain D39 adhesion to A549 cells significantly at 20 µg/well ($p<0.001$). FC peptide inhibited 75% of the unencapsulated strain R6 at 15 µg/well.

Example 5

The Biological Activity of the Flamingo Cadherin Derived Peptide In Vivo

Figure 4A:
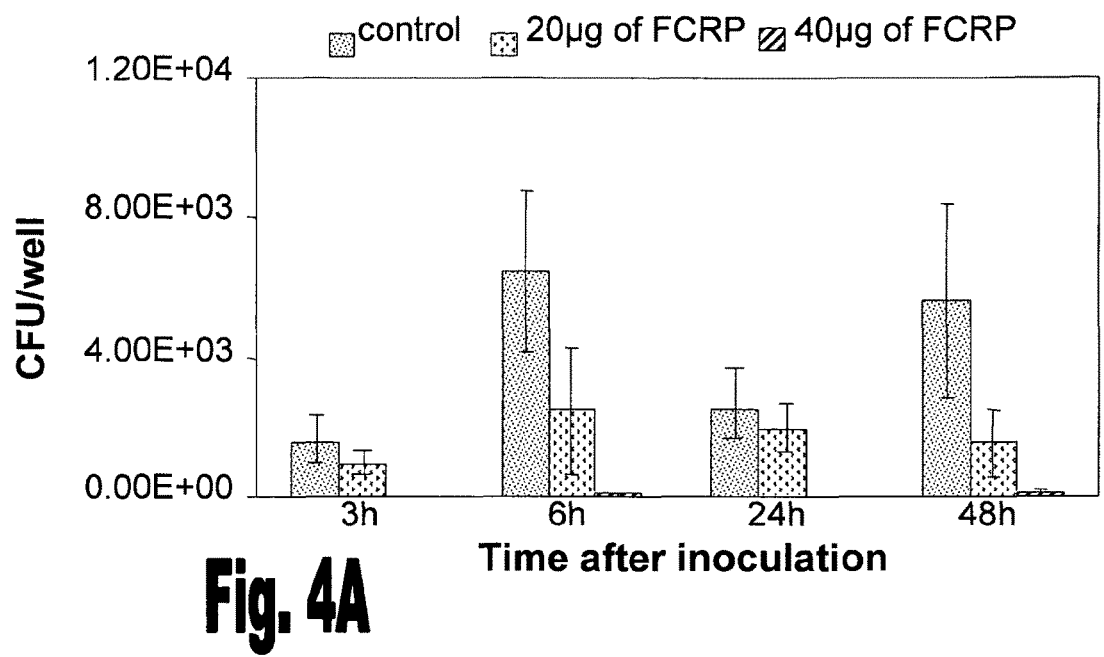
FIGS. 4A and 4B present the results for colonization of a peptide-treated bacterial inoculum of $5 \times 10^5$ cells in the nasopharynx and lungs, respectively.
Figure 4B:
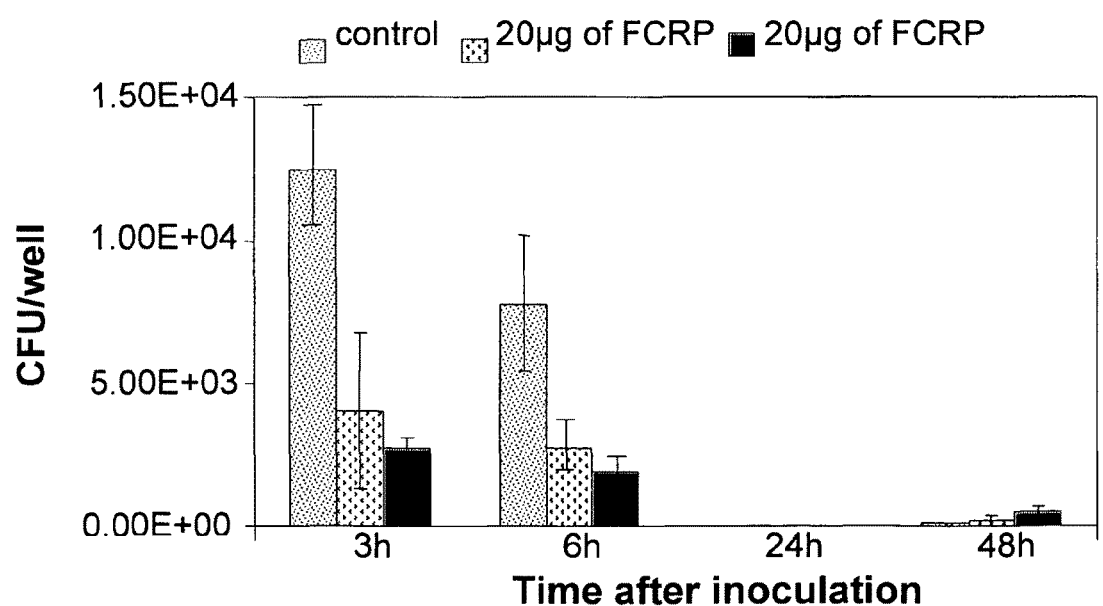

To find whether FC peptide is capable of inhibiting S. pneumoniae colonization, mice were inoculated intranasally prior and after treatment with the FC-derived peptide at the denoted concentration. S. pneumoniae serotype 3, strain WU2 bacteria were treated with FC peptide, excess peptide was removed and the bacteria were inoculated intranasally. Inoculation of the mice with $5\times10^5$ S. pneumoniae treated with 20 µg/ml FC peptide inhibited colonization in the nasopharynx significantly at 3, 6 24 and 48 hours following inoculation ($p<0.01$; FIG. 4A). Treatment of the $5\times10^5$ S. pneumoniae with 40 µg/ml FC peptide prevented S. pneumoniae colonization of the nasopharynx at all time points tested ($p<0.01$; FIG. 4A). Treatment of $5\times10^5$ S. pneumoniae with 20 or 40 µg/ml FC peptide inhibited significantly colonization of the lung at 3 and 6 hours post inoculation ($p<0.001$; FIG. 4B). Using this size of inoculum, a natural clearance of bacteria from the lungs occurred 24 hours and 48 hours following inoculation.

Figure 4C:
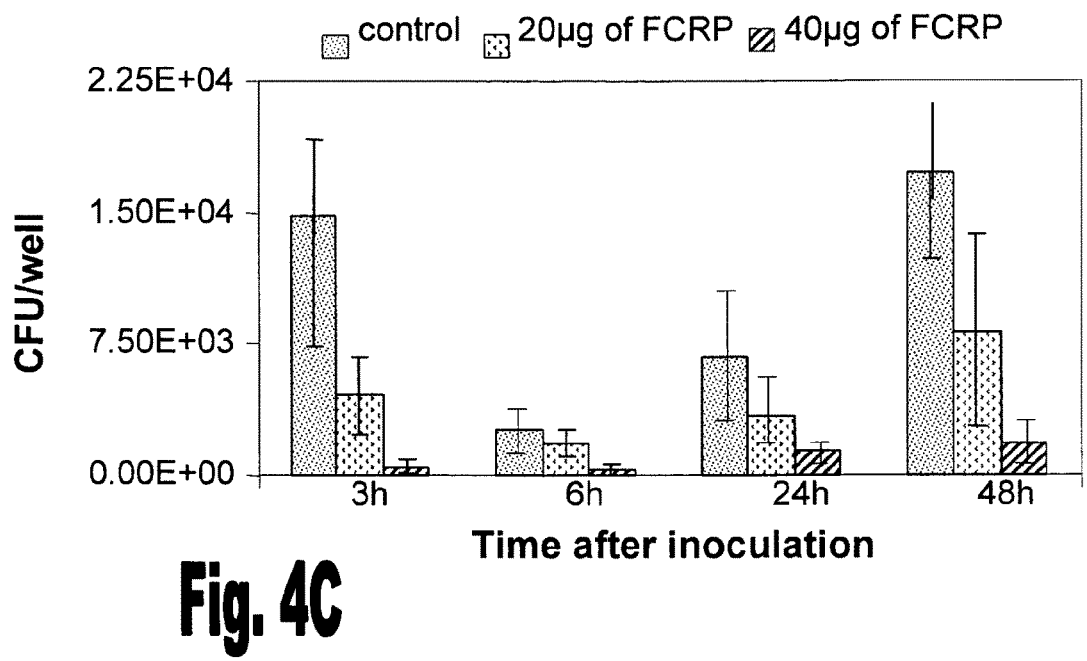
FIGS. 4C and 4D similarly present the results for colonization of a peptide-treated bacterial inoculum of $10^6$ cells in the nasopharynx and lungs, respectively. Moreover, this treatment prevented the development of pneumonia.
Figure 4D:
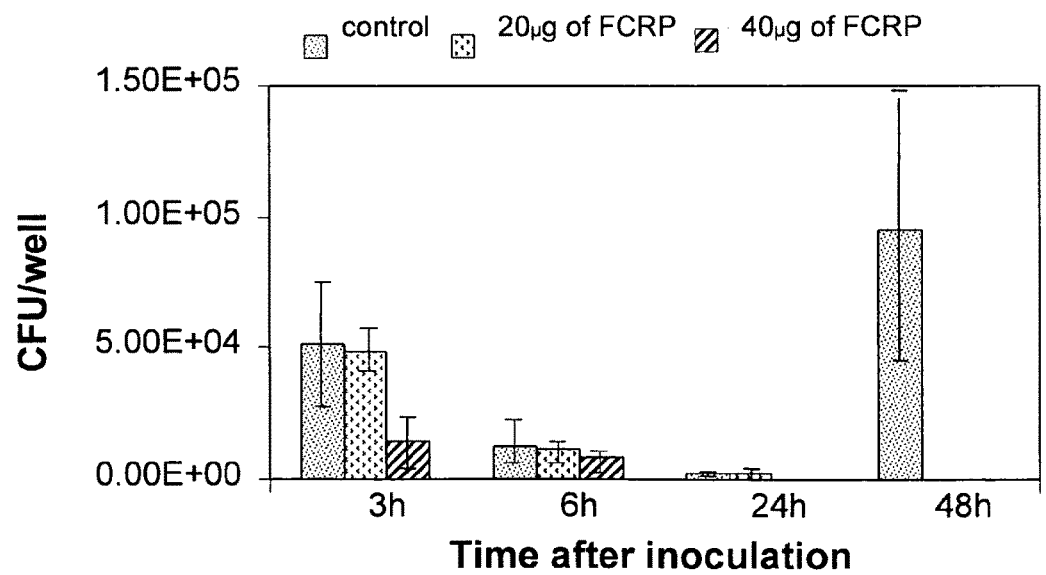

A similar experiment was also performed with a higher initial inoculum. Inoculation of the mice with $10^6$ S. pneumoniae serotype 3 strain WU2 treated with 20 µg/ml FC inhibited colonization in the nasopharynx significantly at 3, 6 24 and 48 hours following inoculation ($p<0.05$; FIG. 4C). Treatment of this inoculum size with 40 µg/ml FC peptide demonstrated a significantly higher ability to inhibit S. pneumoniae colonization of the nasopharynx ($p<0.01$; FIG. 4C). Treatment of $10^6$ S. pneumoniae with 40 µg/ml FC peptide significantly inhibited colonization of the lung at 3, 6 and 24 hours post inoculation ($p<0.05$; FIG. 4D). However, 48 hours post inoculation, while a significant increase in bacterial numbers could be found in mice inoculated with untreated bacteria, signifying the development of pneumonia, no bacteria could be detected in the lungs of mice inoculated with 20 or 40 µg/ml FC peptide-treated bacteria ($p<0.001$; FIG. 4D).

Treatment of bacteria with an unrelated (PsipD) full length protein did not significantly inhibit bacterial adhesion in a dose dependent manner (data not shown).

Figure 4E:
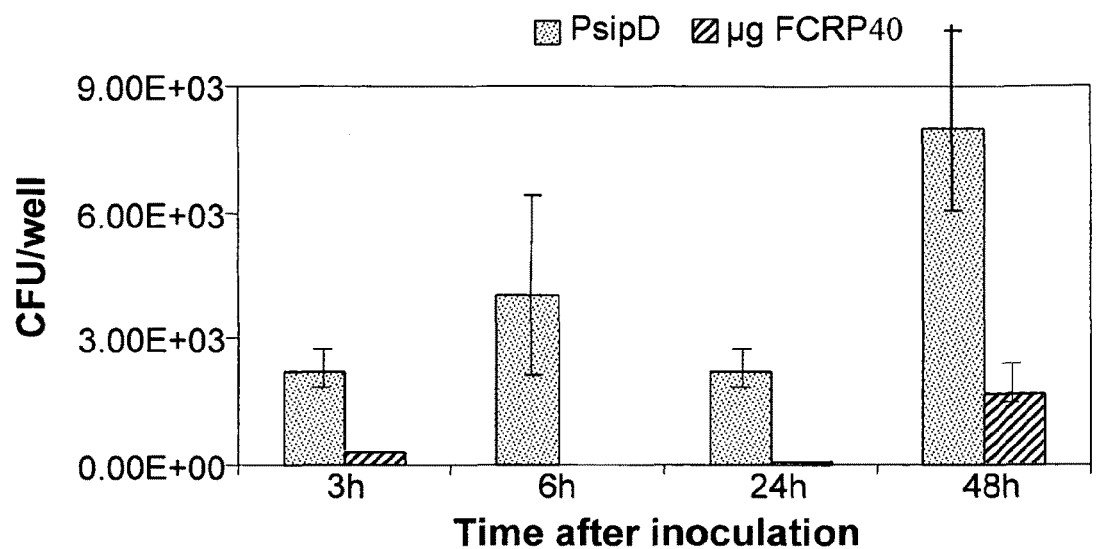
FIGS. 4E and 4F are similar experiments as 4C and 4D but in the control experiments S. pneumoniae were treated with PsipD, a bacterial protein not involved in adhesion, which did not affect bacterial adhesion while FCRP inhibited significantly nasopharyngeal and lung colonization.
Figure 4F:
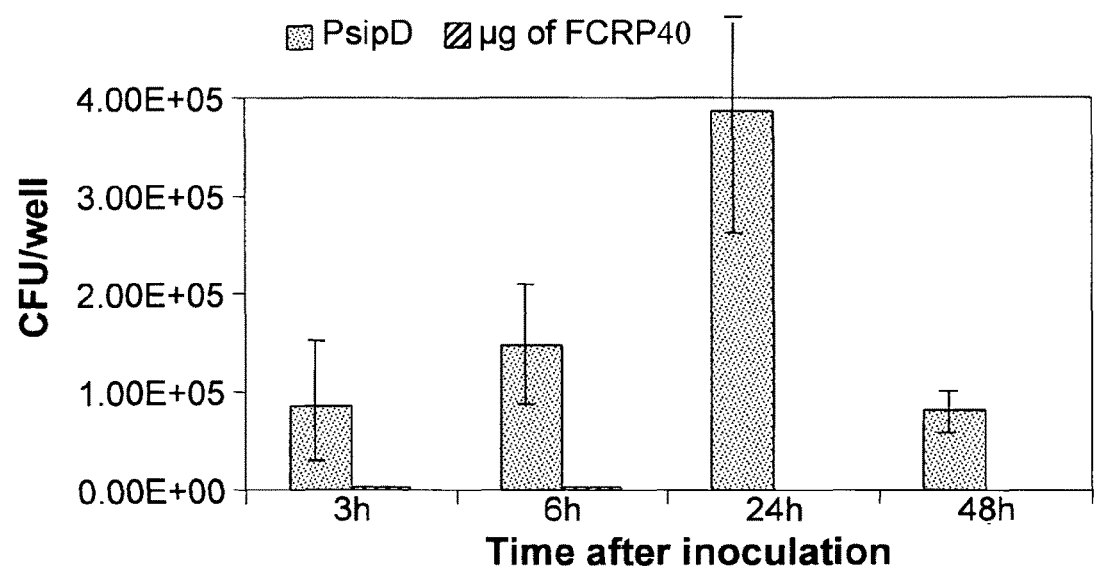

FCRP inhibited bacterial colonization in the nasopharynx (FIG. 4E) and the lungs (FIG. 4F) significantly ($p<0.05$) in comparison to bacteria treated with the unrelated protein rPsipD.

Example 6

Figure 5A:
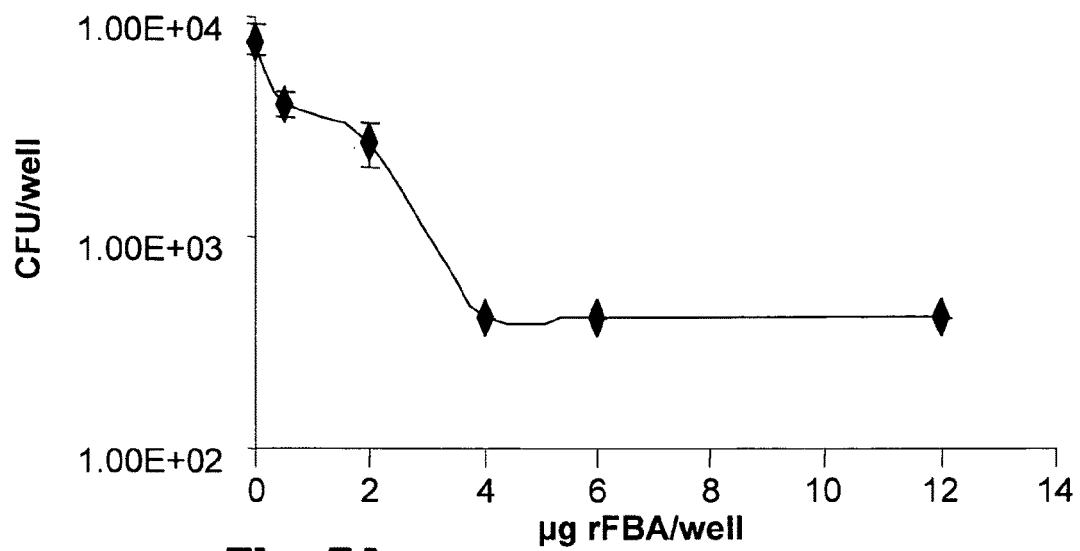
FIG. 5 graphically illustrates the inhibitory effect of recombinant FBA on the adhesion of S. pneumoniae strains WU2 (FIG. 5A) 3.8DW (FIG. 5B) to cultured A549 lung carcinoma cells.
FIG. 5C demonstrates that unrelated protein PsipD is unable to inhibit bacterial adhesion.
Figure 5B:
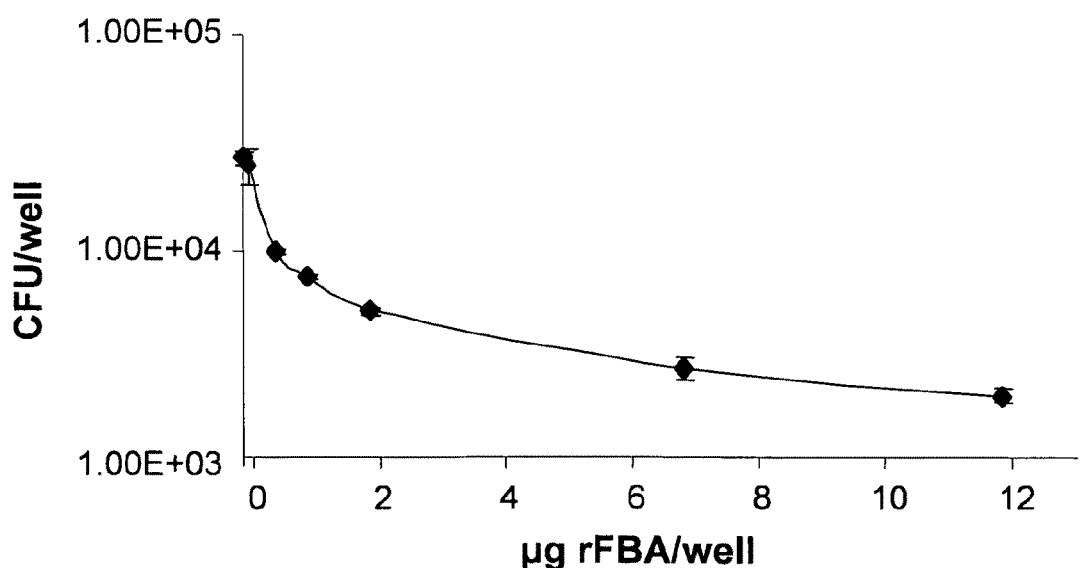
Figure 5C:
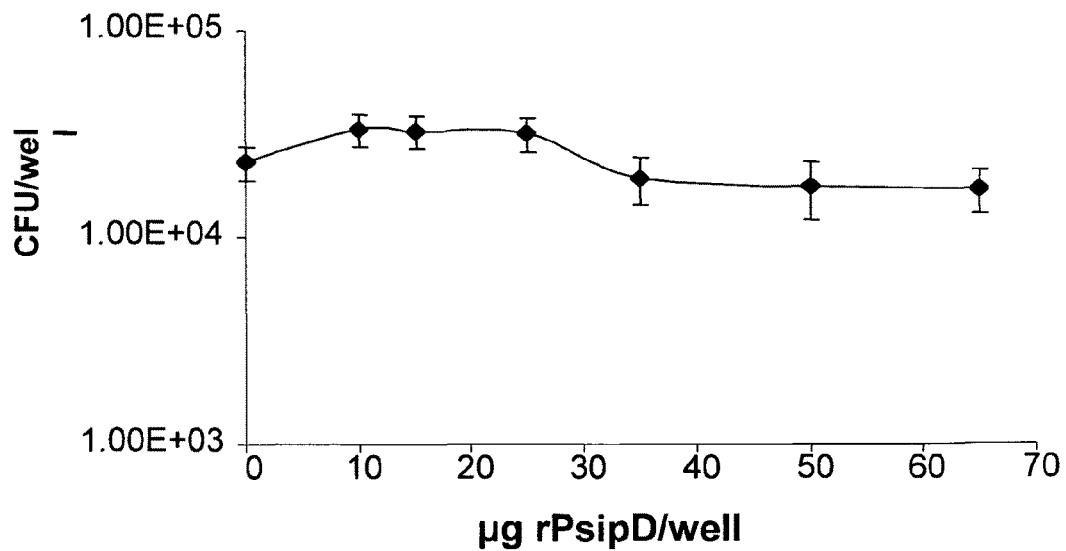

Inhibition of S. pneumoniae Adhesion to A549 Lung Carcinoma Cells by rFBA rFBA, at the indicated concentrations, was added to cultured A549 lung carcinoma cells. Following incubation the excess protein was removed and S. pneumoniae were added to the cells. Excess bacteria were removed and the cells were released, plated onto blood agar plates and the adhered bacteria were enumerated. rFBA inhibited S. pneumoniae encapsulated serotype 3 strain WU2 and its unencapsulated mutant 3.8DW adhesion significantly in a concentration dependent manner ($r=-0.712$; $p<0.001$ and $r=-0.646$, $p<0.001$, respectively). rFBA inhibited 63% of S. pneumoniae strain WU2 adhesion significantly at 0.5 µg/well ($p<0.001$) and 92% of S. pneumoniae strain 3.8 DW at 12 µg/well ($p<0.001$; FIGS. 5A and 5B respectively). Inhibition of encapsulated serotype 3 strain WU2 adhesion to A549 cells was obtained only at 40 µg/ml of PsipD (an unrelated bacterial protein) with a low correlation ($r=-0.419$; $p<0.001$; FIG. 5C). These results differed significantly from the inhibition of the bacteria adhesion with rFBA ($p<0.001$).

Example 7

Inhibition of Encapsulated *S. pneumoniae* Adhesion to A549 Lung Carcinoma Cells with Anti rFBA Antibodies

Figure 6A:
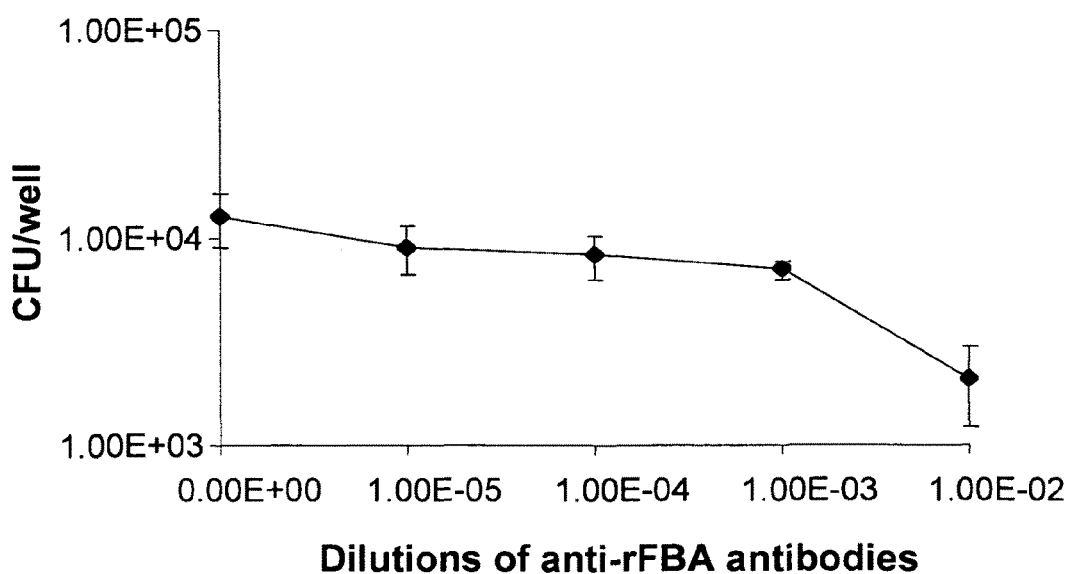
FIG. 6 graphically illustrates the concentration-dependent inhibitory effect of anti rFBA antibodies (present in immunized rabbit sera) on the adhesion of S. pneumoniae strains WU2 (6A) and 3.8 (6B) to cultured A549 cells.
FIG. 6C demonstrates that anti-PsipD antibodies are unable to inhibit bacterial adhesion.
Figure 6B:
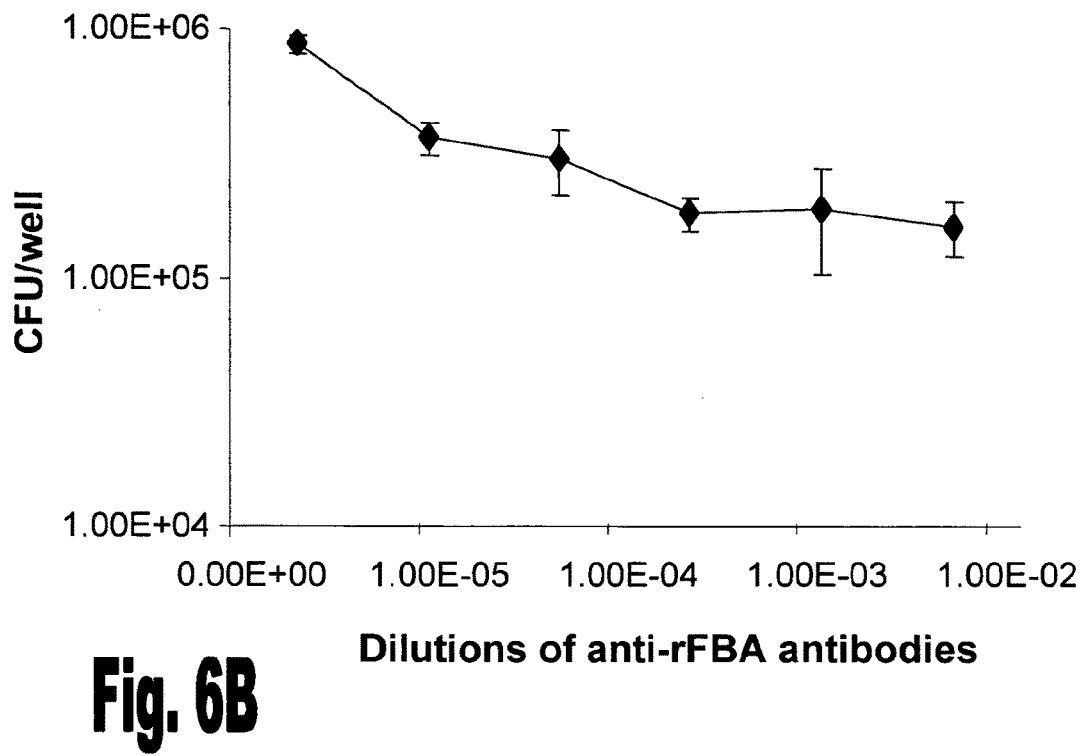
Figure 6C:
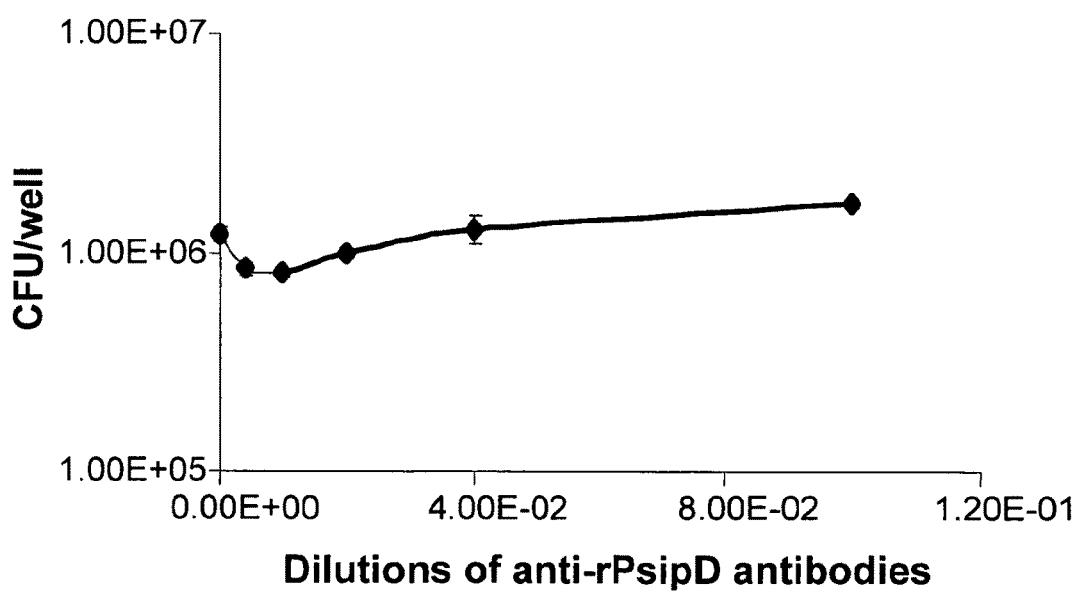

*S. pneumoniae* serotype 3, strains WU2 and 3.8DW, were treated with serum obtained from immunized rabbits, and with preimmune sera as controls at the indicated concentrations. The excess sera were removed following incubation by centrifugation. No effect on bacterial viability was observed with either the immune or the preimmune sera. The assay for inhibition of *S. pneumoniae* adhesion to cultured cells was performed as described in the materials and methods section hereinabove. Anti rFBA antibodies inhibited *S. pneumoniae* strains WU2 and 3.8 adhesion to A549 cells significantly in a concentration dependent manner (r=−0.884, p<0.001 and r=−0.841, p<0.001, respectively; FIGS. 6A and 6B). No effect on the A549 cells viability was observed with either the preimmune or immune sera at the dilutions used in these experiments (data not shown). Anti-PsipD antibodies did not affect bacterial adhesion to 549 cells significantly (r=0.159; p<0.603; FIG. 6C). Notably, none of the sera influenced bacterial viability (no serum $6.8 \times 10^4 \pm 2900$, pre-immune serum $6.9 \times 10^4 \pm 3300$, and immune serum $7.1 \times 10^4 \pm 3500$ CFU).

Example 8

Figure 8:
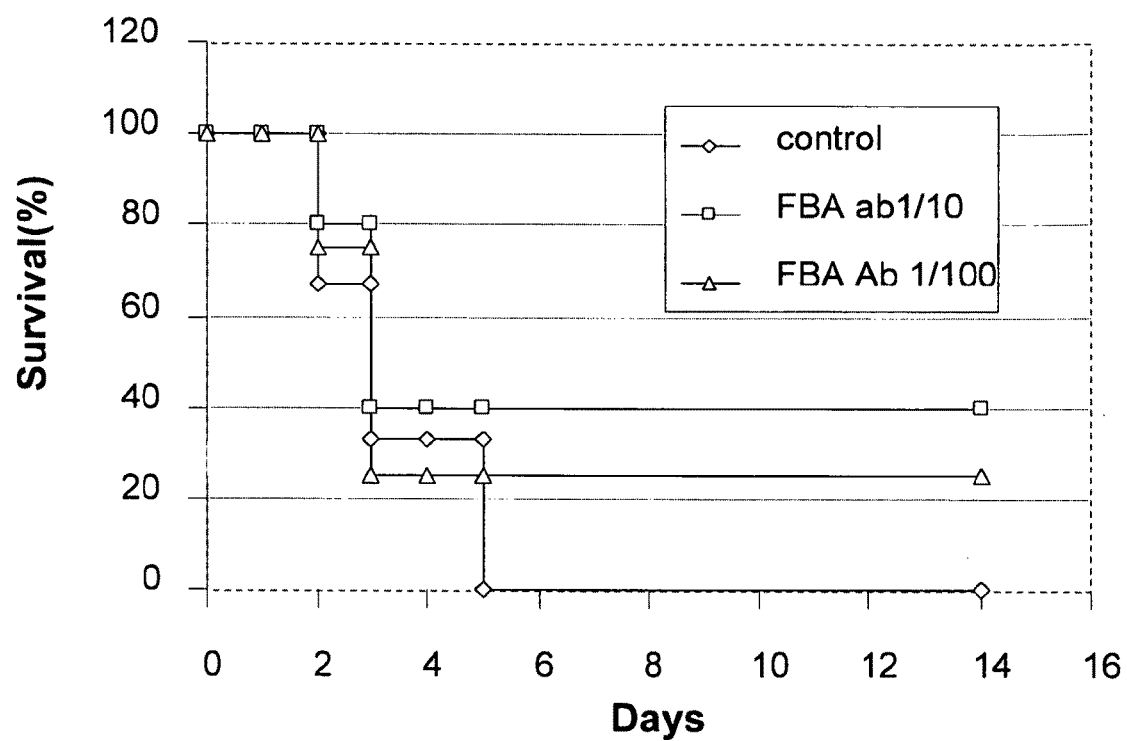
FIG. 8 graphically illustrates the protective ability of anti rFBA antibodies in vivo in mice. Mice were inoculated intranasally with PBS treated bacteria and bacteria treated with ⅒ and 1/100 dilution of rabbit derived anti rFBA antibodies.

*S. pneumoniae* Reduced Virulence Upon Treatment with Antibodies to rFBA In Vivo 7 weeks old BALB/c mice were inoculated intranasally with PBS treated bacteria and bacteria treated with 1/10 and 1/100 dilution of rabbit derived anti rFBA antibodies. While animals inoculated with the PBS succumbed within 5 days, a significant increase (p<0.05) in survival were obtained in mice inoculated with 1/10 or 1/100 dilution of the anti rFBA antibodies (40% and 20% respectively). The results are shown in FIG. 8, where the abscissa indicates the time (in days) following administration of the antibodies and the ordinate indicates percentages of survival of the mice.

Example 9

The Ability of Flamingo Cadherin Receptor Derived Peptide (Abbreviated FCRP and Identified in SEQ ID NO 2) to Inhibit *S. pneumoniae* Colonization and Pneumonia Development The ability of FCRP to interfere in nasopharyngeal colonization and aspiration to the lungs was tested in the intranasal inoculation mouse model, prior to the time of and following inoculation of the mice.

Figure 9:
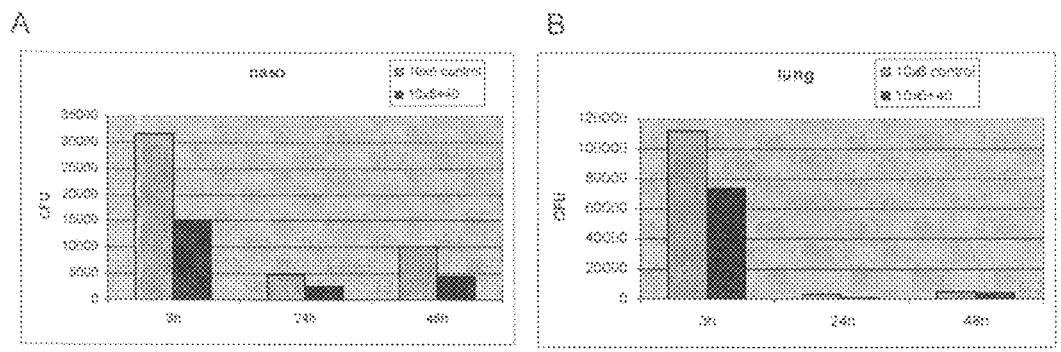
FIG. 9 shows the results of experiments performed in order to demonstrate the ability of FCRP to inhibit colonization and aspiration of S. pneumoniae to the lung. S. pneumoniae serotype 3 strain WU2 ($10^6$ bacteria) were treated ex vivo for 1 hr with 40 µg synthetic FCRP and then inoculated intranasally to 7 weeks old BALB/c mice (control n=9 FCRP n=9). At 3, 24 and 48 hours following inoculation the nasopharynx and the lungs were excised, homogenized and plated onto blood agar plates.

Seven week old BALB/c female mice were anaesthetized with Isoflurane (R$_x$Elite, Meridian, Id.) and inoculated intranasally with *S. pneumoniae* serotype 3 strain WU2 ($10^6$ bacteria in 25 μl PBS, a highly virulent bacterial strain) after treatment with 40 μg synthetic Flamingo cadherin receptor derived peptide (FCRP) for 1 hr. At 3, 24 and 48 hours following inoculation the nasopharynx, the lungs were excised, homogenized and plated onto blood agar plates (FIG. 9A). This preparation of FCRP inhibited nasopharyngeal colonization significantly (p<0.05). Similarly, a significant inhibition of aspiration to the lungs could be observed (FIG. 9B). In FIG. 9 (and also in the following figures), the left bar in each two or three coupled bars indicates the results for the control experiment.

Figure 10:
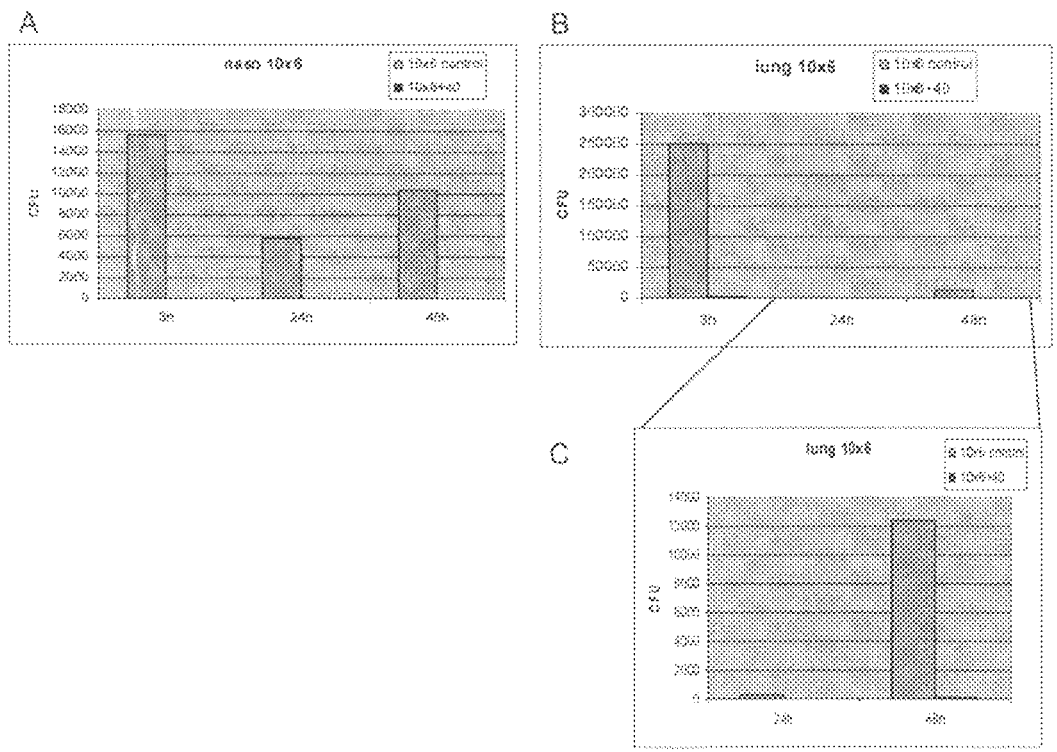
FIG. 10 shows the results of experiments performed in order to demonstrate that FCRP inhibits pneumoniae development. S. pneumoniae serotype 3 strain WU2 ($10^6$ bacteria) were treated ex vivo for 1 hr with 40 µg synthetic FCRP and then inoculated intranasally to 7 weeks old BALB/c mice (control n=9 FCRP n=9). At 3, 24 and 48 hours following inoculation the nasopharynx and the lungs were excised, homogenized and plated onto blood agar plates.

In an additional experiment a new preparation of synthetic FCRP was tested. In this experiment a different frozen batch of the bacteria was used, in attempt to cause pneumonia development. This batch of bacteria was recalibrated (data not presented) and found to cause pneumonia namely, an increase in bacteria number in the lungs 48 h following inoculation could be found. In this experiment the peptide prevented completely nasopharyngeal colonization and aspiration of the bacteria to the lungs (FIGS. 10A and 10B; p<0.001)). Moreover, while in control animal an increase in bacterial load in the lungs was found 48 hr following inoculation, no bacteria could be found in the lungs of mice inoculated with peptide treated bacteria (FIG. 10 C; p<0.001; the Y-axis was adjusted to demonstrate the load observed in this case).

Figure 11:
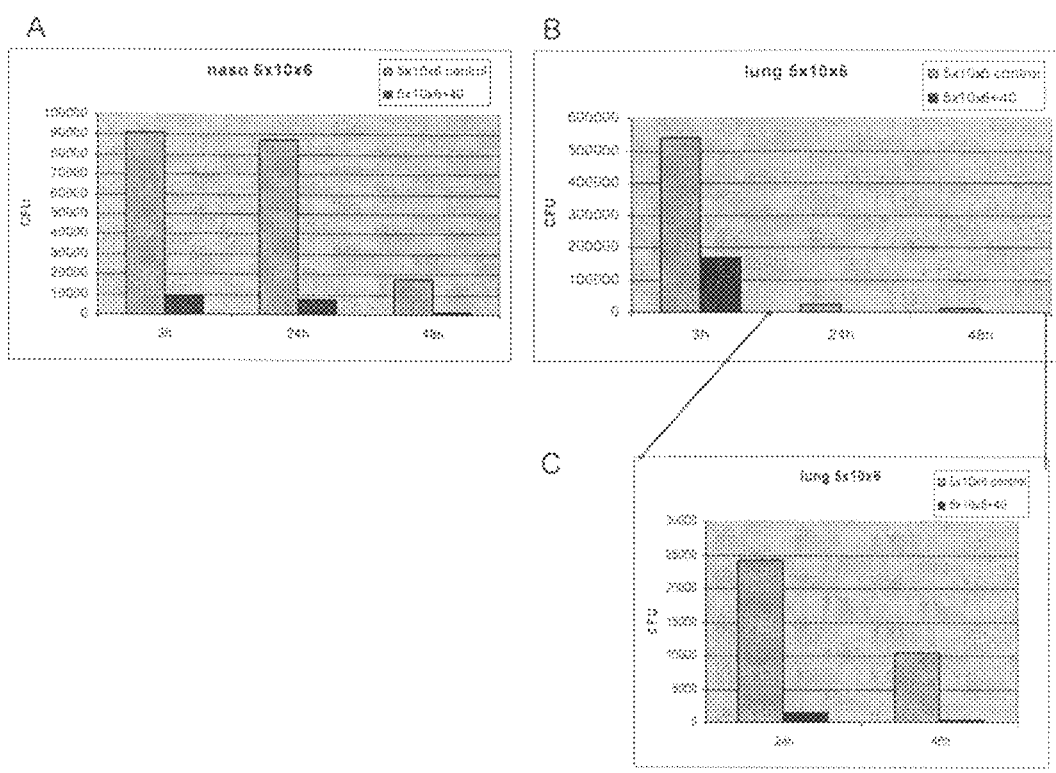
FIG. 11 shows the results of experiments performed in order to demonstrate that FCRP inhibits pneumoniae development. S. pneumoniae serotype 3 strain WU2 ($5\times10^6$ bacteria) were treated ex vivo for 1 hr with 40 µg synthetic FCRP and then inoculated intranasally to 7 weeks old BALB/c mice. At 3, 24 and 48 hours following inoculation the nasopharynx, the lungs were excised, homogenized and plated onto blood agar plates (n=9 in each group).

A similar experiment was performed with a higher number of bacteria in the inoculation ($5 \times 10^6$) and similar results were obtained (FIG. 11). A significant inhibition of bacterial colonization (FIG. 11A; p<0.001), reduced aspiration to the lung (FIG. 11B; p<0.001) and reduced pneumonia development (FIG. 11C; p<0.001; the Y-axis was adjusted to demonstrate the load observed in this case).

Figure 12:
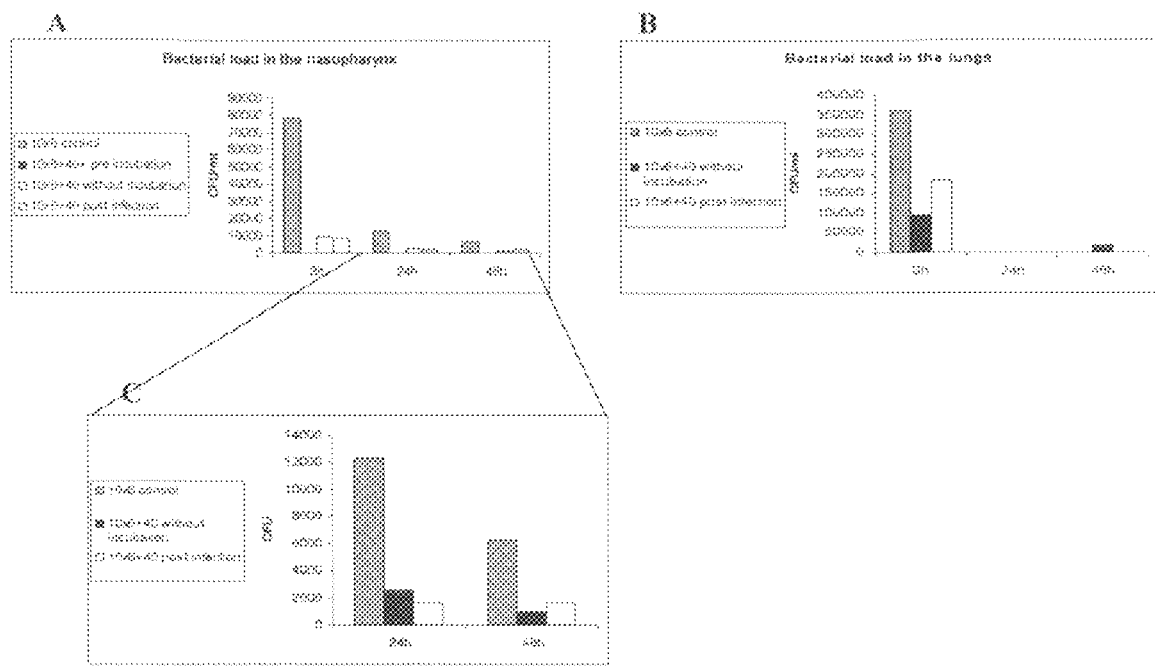
FIG. 12 shows the results of post inoculation treatment with FCRP. FCRP was either administrated 1 hr post inoculation or co administered at the time of intranasal bacterial inoculation and these in comparison intranasal inoculation of bacteria pre treated for 1 hr with the FCRP peptide (n=9 in each group).

To evaluate the ability of the FCRP to treat infection, mice were inoculated intranasally as described above and the peptide was either co-administrated with the bacteria or FCRP was administrated intranasally 1 hr after bacterial inoculation and the extent of colonization was tested 3 hours later. In both cases the bacterial load was tested 4 hr following bacterial inoculation. The reduction of bacterial load in the nasopharynx was significant and no significant difference could be found in the case of co-administration of the FCRP or the post administrated FCRP in the nasopharynx (FIGS. 12A and 12C; p<0.001; the Y-axis was adjusted to demonstrate the load observed in this case). The number of bacteria in the lungs 4 hours after inoculation in the case of co-administration of the bacteria and peptides or 3 hours after peptide treatment (1 hr after bacterial inoculation) was reduced significantly (p<0.05). However, in this experiment the bacteria were cleared from the lungs in both the treated and non treated mice (FIG. 12B).

Figure 13:
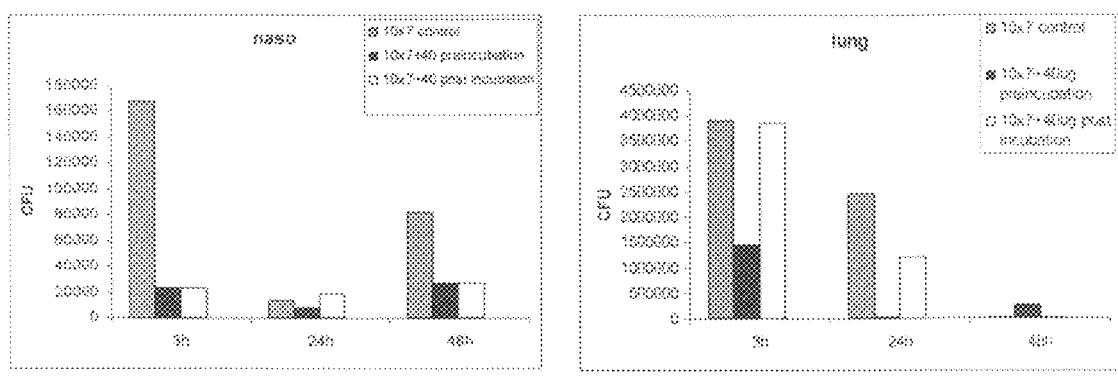
FIG. 13 shows that FCRP inhibits high dose of bacterial infection. BALB/c mice were inoculated intranasally with $10^7$ S. pneumoniae serotype 3 strain WU2 prior or after treatment with 40 µg of FCRP. The nasopharynx and the lungs were excised homogenized and plated onto blood agar plates at 3, 24 and 48 hour following inoculation (n=9 in each group).

The bacterial inoculum was increased to the sublethal level of $10^7$ bacteria. Even at these high doses, pre-treatment or one FCRP post inoculation treatment reduced bacterial load significantly at 3 and 48 hrs after inoculation (FIG. 13A, p<0.001). The initial aspiration to the lungs occurs at the awakening time of the mouse which occurs minutes after the inoculation at this inoculum size. In this case a clear reduction in bacterial load was observed 24 hour following inoculation in both groups (FIG. 13B; p<0.05).

Example 10

Figure 14:
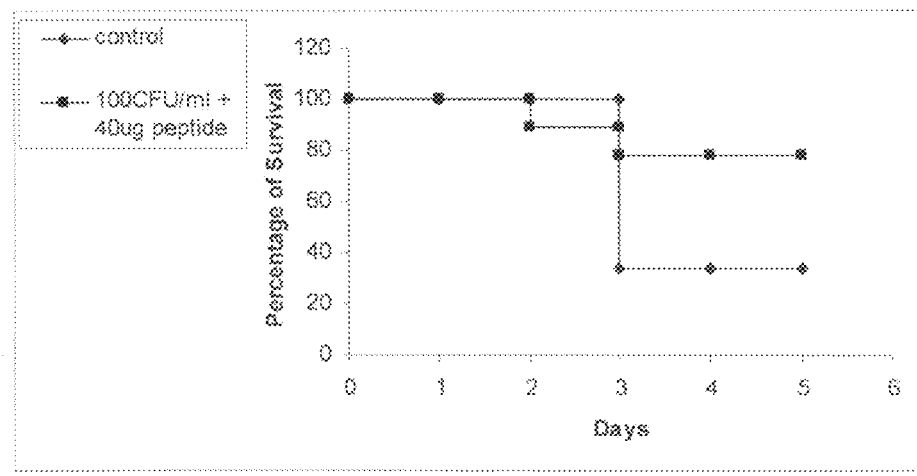
FIG. 14 illustrates percent survival of mice inoculated intraperitonealy with a lethal dose of S. pneumoniae prior to or after treatment with FCRP in a mouse model for sepsis. Seven weeks old BALB/c mice were inoculated intraperitoneal with a lethal dose (100 CFU) of S. pneumoniae serotype 3 strain WU2 prior and after ex-vivo treatment with FCRP (n=9 in each group).

The Ability of Flamingo Cadherin Receptor Derived Peptide (Abbreviated FCRP and Identified in SEQ ID NO 2) to Inhibit *S. pneumoniae* Systemic Infection 1) A lethal dose of *S. pneumoniae* serotype 3 strain WU2 (100 CFU) was used in this experiment. Bacteria were either untreated or treated ex-vivo for 1 hr with FCRP and used to inoculate intraperitoneally 7 weeks old BALB/c mice. FIG. 14, where the survival rate is plotted against time, shows that pretreatment of the bacteria with FCRP increased the survival rate of the mice significantly (p<0.05).

Figure 15:
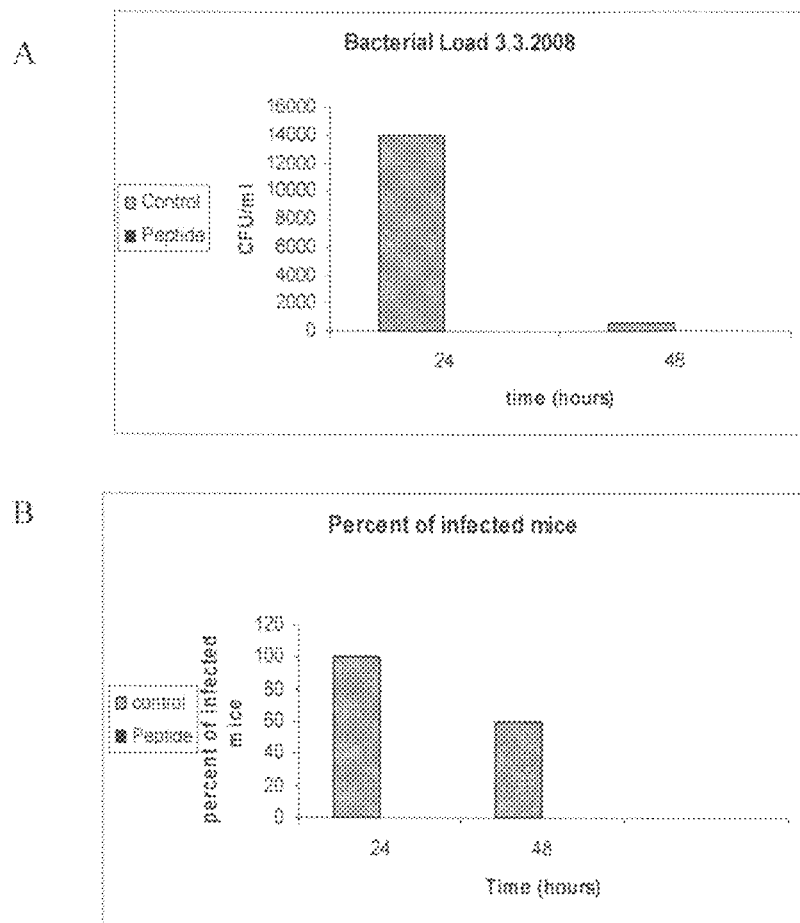
FIG. 15 shows the ability of FCRP to inhibit bacterial load in the spleen during systemic infection. A lethal dose of S. pneumoniae serotype 3 strain WU2 (100 CFU) were inoculated intraperitoneally to 7 weeks old BALB/c mice in the presence and absence of FCRP. 24 and 48 hr later the mice were eutinized and the spleens were excised, homogenized and plated onto blood agar plates.

2) A lethal dose of *S. pneumoniae* serotype 3 strain WU2 (100 CFU) was used in this experiment. Bacteria were co-administered intraperitonealy to 7 weeks old BALB/c mice in the presence and absence of FCRP. Mice inoculated with bacteria in the absence of the peptide demonstrated high levels of bacteria load in the spleens 24 hours following inoculation (FIG. 15A). Furthermore, in mice infected in the absence of FCRP bacteria could be found in the spleens of 100% of the (FIG. 15B) mice. In this experiment no bacteria could be recovered from the spleens of mice inoculated with bacteria in the presence of the FCRP (FIG. 15B).

Figure 16:
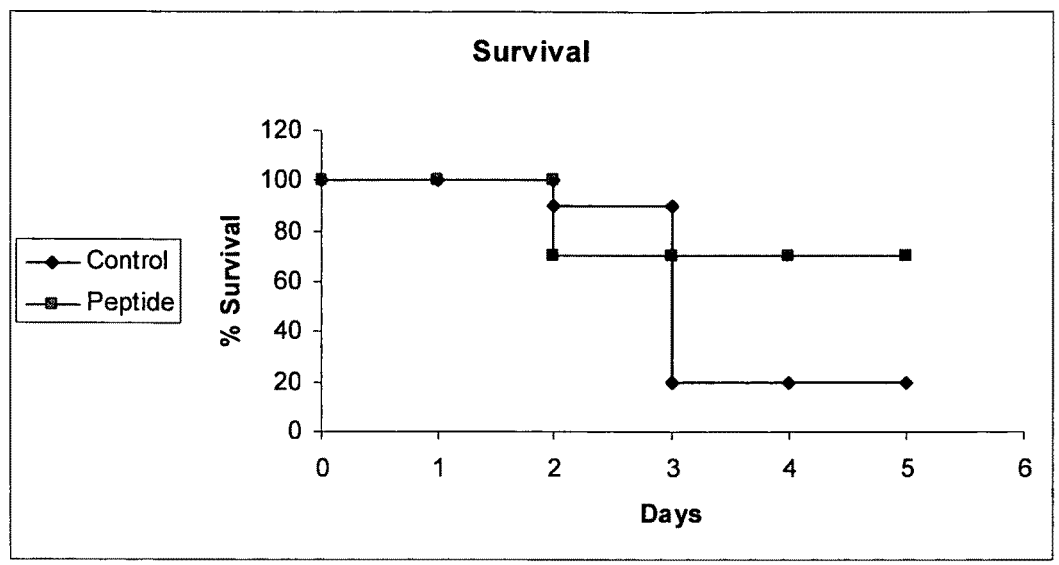
FIG. 16 shows the percent survival of mice inoculated in absence and presence of FCRP. Mice were inoculated intraperitonealy with a lethal dose of S. pneumoniae in the presence and absence of FCRP and survival was monitored daily (n=9 in each group).

3) In a similar experiment, the mice were inoculated with bacteria in the presence and absence of FCRP and the mice were monitored for their survival. A significant increase in survival could be observed in the group of mice in which co-administration of bacteria and FCRP (p<0.001; FIG. 16) was performed.

Summary:

FCRP was shown to interfere in bacterial infectivity in the case of bacteria treated ex-vivo with the peptide, in the case that FCRP was co-administered with the bacteria and in the case that FCRP was administered 1 hr after intranasal inoculation. The inhibition of bacterial infectivity could be achieved using increasing bacterial numbers, up to $10^7$ bacteria in the inoculum. Moreover, FCRP increased survival rates of mice following administration of a lethal dose of *S. pneumoniae* intraperitonealy, which represents an acceptable model of systemic infection resembling sepsis. This was demonstrated using different preparations of the FCRP and different bacterial batches, which were found in the laboratory to vary in their virulence.

The ability of FCRP to reduce bacterial infectivity was tested when inoculated intraperitonealy without prior treatment of the bacteria. Specifically, the effect of FCRP on bacterial load, the number of infected mice and mice survival was tested. In all cases a significant reduction of infectivity could be demonstrated in mice co-administered intraperitonealy with *S. pneumoniae* in the presence of FCRP.

The invention claimed is:

1. A composition comprising the one or more peptides selected from the group consisting of:

(SEQ ID NO 1)
a) Asp-Ser-Asp-Ser-Asp-Ser-Asp-Leu-Ser-Leu-Glu-Olu-Glu;

(SEQ ID NO 2)
b) Ala-Asp-Ser-Asp-Ser-Asp-Ser-Asp-Leu-Ser-Leu-Glu-Glu-Glu-Arg.

2. The composition according to claim 1, wherein said composition comprises a single peptide of the sequence:

(SEQ ID NO 2)
Ala-Asp-Ser-Asp-Ser-Asp-Ser-Asp-Leu-Ser-Leu-Glu-Glu-Glu-Arg.

3. An isolated peptide consisting of the following sequence:

(SEQ ID NO: 1)
Asp-Ser-Asp-Ser-Asp-Ser-Asp-Leu-Ser-Leu-Glu-Glu-Glu.

4. An isolated peptide of consisting the following sequence:

(SEQ ID NO: 2)
Ala-Asp-Ser-Asp-Ser-Asp-Ser-Asp-Leu-Ser-Leu-Glu-Glu-Glu-Arg.

5. A method of treating a patient for *S. pneumonia* infection, the method comprising administering to the patient a composition according to claim 1.

* * * * *